US010832579B2

(12) United States Patent
Patel

(10) Patent No.: US 10,832,579 B2
(45) Date of Patent: Nov. 10, 2020

(54) INTEGRATED AMBULANCE TRACKING SYSTEM

(71) Applicant: Accenture Global Solutions Limited, Dublin (IE)

(72) Inventor: Mehul Patel, Bangalore (IN)

(73) Assignee: Accenture Global Solutions Limited, Dublin (IE)

( * ) Notice: Subject to any disclaimer, the term of this patent is extended or adjusted under 35 U.S.C. 154(b) by 341 days.

(21) Appl. No.: 15/588,064

(22) Filed: May 5, 2017

(65) Prior Publication Data

US 2017/0344707 A1  Nov. 30, 2017

(30) Foreign Application Priority Data

May 31, 2016  (IN) .............................. 201641018607

(51) Int. Cl.
*G08G 1/00* (2006.01)
*G16H 40/20* (2018.01)

(52) U.S. Cl.
CPC ............. *G08G 1/202* (2013.01); *G16H 40/20* (2018.01)

(58) Field of Classification Search
CPC combination set(s) only.
See application file for complete search history.

(56) References Cited

U.S. PATENT DOCUMENTS

| 3,638,179 | A * | 1/1972 | Coll et al. |
| 9,494,938 | B1 * | 11/2016 | Kemler et al. |
| 2004/0034284 | A1 * | 2/2004 | Aversano et al. |
| 2009/0224889 | A1 * | 9/2009 | Aggarwal et al. |
| 2010/0305970 | A1 * | 12/2010 | McLaren et al. |
| 2013/0073302 | A1 * | 3/2013 | Ryan et al. |
| 2013/0179188 | A1 * | 7/2013 | Hyde et al. |
| 2014/0203909 | A1 * | 7/2014 | Elgebaly et al. |
| 2015/0227463 | A1 * | 8/2015 | Byers et al. |
| 2016/0063658 | A1 * | 3/2016 | Breazeale |
| 2016/0275151 | A1 * | 9/2016 | Lovati et al. |
| 2017/0108342 | A1 * | 4/2017 | Foreman et al. |
| 2017/0251347 | A1 * | 8/2017 | Mehta et al. |
| 2017/0325056 | A1 * | 11/2017 | Mehta et al. |
| 2017/0372029 | A1 * | 12/2017 | Saliman et al. |
| 2018/0090231 | A1 * | 3/2018 | Liederman et al. |

* cited by examiner

Primary Examiner — Michael Tomaszewski
Assistant Examiner — William T. Monticello
(74) Attorney, Agent, or Firm — Harrity & Harrity, LLP

(57) ABSTRACT

A system may receive, from a first device associated with a patient, a request for an ambulance. The system may determine, based on a location associated with the first device, an available ambulance to be dispatched to the patient. The system may provide, to a second device associated with an ambulance operator of the available ambulance, information that identifies the location associated with the first device. The system may identify a hospital to which the patient is to be delivered. The system may provide, to a third device associated with the hospital, information associated with the available ambulance or the patient.

20 Claims, 30 Drawing Sheets

500

600

700

Sign Up

First Name *

Mehul

Last Name *

Patel

Patient ID

C1234098756

Mobile Phone Number 9687 326 300

User ID * mmpatel

Password *

••••••••

Re-enter Password *

Emergency Contact
We will use your contact details to notify them for emergency purposes.

Family Doctor Name

Doctor's Contact Number

Emergency Contact Name

Contact Number

Health Details

Are you allergeic to any medication?

[ Medicine name ]

Do you have any pre-existing health conditions?

[ Select one ▼ ]

What is your Electronic Health Record (EHR) Number?

Patient Details

Name
Mehul Patel

Age
35

Blood Group
A Plus

Medication
Medicine name, medicine name...

Last Treated Doctor
Venkat Sundar

Family Doctor
Dr. Sudha Krishnan

PROCEED

INTEGRATED AMBULANCE TRACKING SYSTEM

RELATED APPLICATION

This application claims priority under 35 U.S.C. § 119 to Indian Patent Application No. 201641018607, filed on May 31, 2016, the content of which is incorporated by reference herein in its entirety.

BACKGROUND

An ambulance is a vehicle for transportation of sick or injured people to, from, or between places of treatment for an illness or injury. In some cases, an ambulance may transport equipment to treat illnesses or injuries, and/or may transport medical staff for treating illnesses or injuries.

SUMMARY

According to some possible implementations, a system may include one or more processors. The one or more processors may receive, from a first device associated with a patient, a request for an ambulance. The one or more processors may determine, based on a location associated with the first device, an available ambulance to be dispatched to the patient. The one or more processors may provide, to a second device associated with an ambulance operator of the available ambulance, information that identifies the location associated with the first device. The one or more processors may identify a hospital to which the patient is to be delivered. The one or more processors may provide, to a third device associated with the hospital, information associated with the available ambulance or the patient.

According to some possible implementations, a non-transitory computer-readable medium may store one or more instructions that, when executed by one or more processors, cause the one or more processors to receive, from a first device associated with a user, a request for a vehicle. The one or more instructions may cause the one or more processors to determine, based on a location associated with the first device, an available vehicle to be dispatched to the user. The one or more instructions may cause the one or more processors to provide, to a second device associated with a driver of the available vehicle, information that identifies a traffic route to the first device. The one or more instructions may cause the one or more processors to identify a destination to which the user is to be delivered. The one or more instructions may cause the one or more processors to provide, to a third device associated with the destination, information associated with the available vehicle or the user.

According to some possible implementations, a method may be performed by a system that includes one or more devices. The method may include receiving, by the system and from a patient device associated with a patient, a request for an ambulance. The method may include determining, by the system and based on a location of the patient device, an available ambulance to be dispatched to the patient. The method may include providing, by the system and to an ambulance operator device associated with an ambulance operator of the available ambulance, information associated with the location of the patient device. The method may include identifying, by the system, a hospital to which the ambulance is to deliver the patient. The method may include providing, by the system and to a hospital device associated with the hospital, information associated with the available ambulance or the patient

BRIEF DESCRIPTION OF THE DRAWINGS

FIGS. 5-30 are diagrams of example user interfaces used in association with an integrated ambulance tracking system.

DETAILED DESCRIPTION

The following detailed description of example implementations refers to the accompanying drawings. The same reference numbers in different drawings may identify the same or similar elements.

Time is of the essence in emergency situations. For example, the amount of time that it takes an ambulance to pick up a patient and take that patient to a hospital can mean the difference between life and death. Any delays or lack of preparation at the hospital can have similar consequences. Implementations described herein assist in reducing delays and increasing preparedness for patient care by utilizing an integrated ambulance tracking system that enables coordination among devices of a variety of parties associated with patient care, including the patient, an ambulance operator, an ambulance provider (e.g., a caregiver, such as a nurse, doctor, or emergency personnel that travels with an ambulance), police officers (e.g., officers in the field, such as traffic police), a police department, and emergency contacts of the patient (e.g., a family member, a friend, a family doctor, etc.). The integrated ambulance tracking system automatically provides the appropriate information to these various parties at the appropriate time, thereby reducing delays in patient care and ensuring proper preparation for patient care. The integrated ambulance tracking system also conserves network resources and computing resources due to efficiencies associated with ensuring that appropriate information is provided to appropriate devices at appropriate times.

Figure 1:
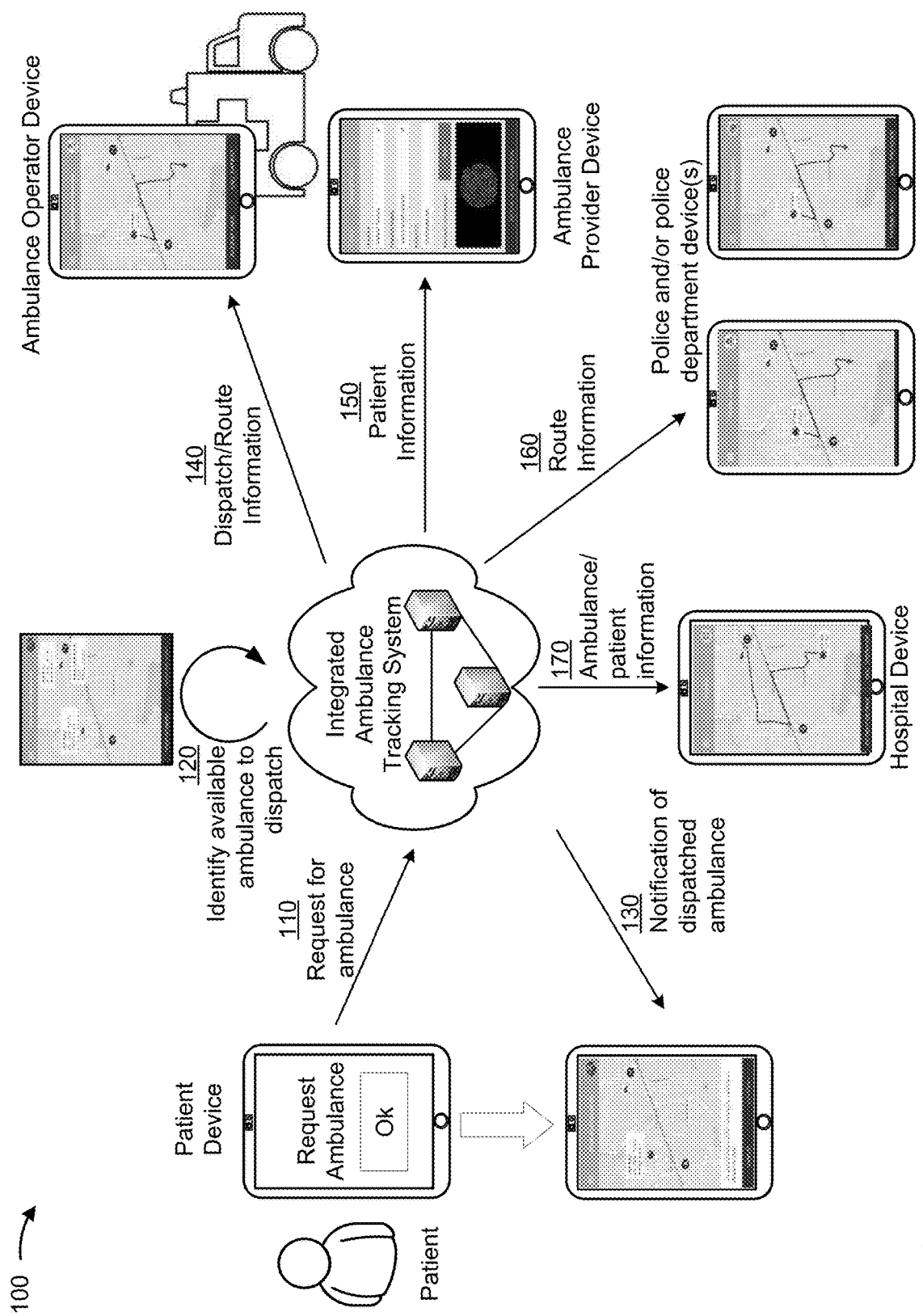
FIG. 1 is a diagram of an overview of an example implementation described herein.

FIG. 1 is a diagram of an overview of an example implementation 100 described herein. As shown in FIG. 1, and by reference number 110, a patient may interact with a patient device (e.g., a mobile device) to request an ambulance. An integrated ambulance tracking system (e.g., one or more servers in a cloud computing environment) may receive the request, and may identify an available ambulance to dispatch to the patient, as shown by reference number 120. For example, the integrated ambulance tracking system may identify an available ambulance, from a set of ambulances, based on a location associated with the patient device (e.g., a geographic proximity between the available ambulance and the location), based on patient selection of an ambulance (e.g., via a user interface of the patient device), based on ambulance operator input (e.g., indicating a confirmation that the ambulance operator is available to pick up the patient), or the like. As shown by reference number 130, the integrated ambulance tracking system may provide, to the patient device, a notification indicating that the available ambulance has been dispatched to the patient.

The integrated ambulance tracking system may further coordinate with a variety of devices to ensure swift pick up of the patient, smooth transition of the patient to the hospital, and appropriate preparation of caregivers. For example, as shown by reference number 140, the integrated ambulance tracking system may provide, to an ambulance operator device (e.g., a mobile device and/or geographic positioning system (GPS) device of an ambulance driver), dispatch information. The dispatch information may identify the fastest route from the current location of the ambulance to the patient. Additionally, or alternatively, the dispatch information may identify the fastest route from the patient's location to the hospital. In some cases, the ambulance may be a self-driving vehicle, and the integrated ambulance tracking system may provide instructions to direct the self-driving vehicle to the patient and/or the hospital. In this way, the integrated ambulance tracking system may assist in reducing delays in patient care and may conserve network resources by providing the appropriate information to the appropriate devices.

As another example, and as shown by reference number 150, the integrated ambulance tracking system may provide patient information to an ambulance provider device (e.g., a mobile device, a computing device in an ambulance, etc.) of an ambulance provider (e.g., a caregiver that travels in the ambulance, such as an emergency medical technician (EMT), an ambulance technician, a nurse, a doctor, or the like). For example, the integrated ambulance tracking system may provide information regarding the medical emergency of the patient, medical records associated with the patient, or the like, to assist an ambulance provider in providing the appropriate care to the patient as quickly as possible. In some implementations, the integrated ambulance tracking system may only provide relevant information to the ambulance provider device, thereby conserving network resources. Additionally, or alternatively, the ambulance may include equipment for providing telemedicine, and the integrated ambulance tracking system may provide appropriate information (e.g., patient information) to this telemedicine equipment to assist with providing more effective and efficient care for the patient.

As another example, and as shown by reference number 160, the integrated ambulance tracking system may provide route information to a police device (e.g., associated with a police officer, such as a traffic police officer or a patrol police officer) and/or to a police department device (e.g., a computing device in a police station or police headquarters). The route information may indicate a route (e.g., a traffic route) to be taken by the ambulance to the patient and/or to the hospital. In this way, police personnel may assist in clearing traffic from the route of the ambulance. In some implementations, the integrated ambulance tracking system may provide instructions to traffic control devices (e.g., traffic signals, devices that control traffic signals, etc.) to instruct the traffic control devices regarding signals to be output (e.g., red lights, green lights, etc.) to allow the ambulance operator to quickly reach the patient and/or the hospital. For example, traffic signals may be interlinked, and the integrated ambulance tracking system may provide instructions to one or more traffic signals to automate signal changing based on ambulance movement on the road, in order to clear a route for the ambulance to a patient and/or a hospital.

As another example, and as shown by reference number 170, the integrated ambulance tracking system may provide ambulance information and/or patient information to a hospital device (e.g., a computing device) associated with a hospital for which the ambulance is destined. For example, the integrated ambulance tracking system may provide a notification that the ambulance will be coming to the hospital, an indication of an estimated time of the ambulance's arrival, information regarding the patient (e.g., based on electronic medical records, information input to the ambulance provider device, information input to the patient device, etc.), or the like. In this way, the integrated ambulance tracking system assists hospital staff with preparing appropriate equipment (e.g., an operating room, a gurney, the appropriate amount and type of blood, surgical equipment, hospital equipment, etc.) based on a medical situation associated with the patient.

Although not shown, in some implementations, the integrated ambulance tracking system may coordinate with other devices. For example, the integrated ambulance tracking system may provide notifications to contact devices (e.g., mobile devices or other computing devices) associated with a family member of the patient, a friend of the patient, a doctor of the patient, or other contacts of the patient. In this way, the integrated ambulance tracking system ensures efficient communication among all parties associated with the patient, and efficient use of network resources.

As indicated above, FIG. 1 is provided merely as an example. Other examples are possible and may differ from what was described with regard to FIG. 1.

Figure 2:
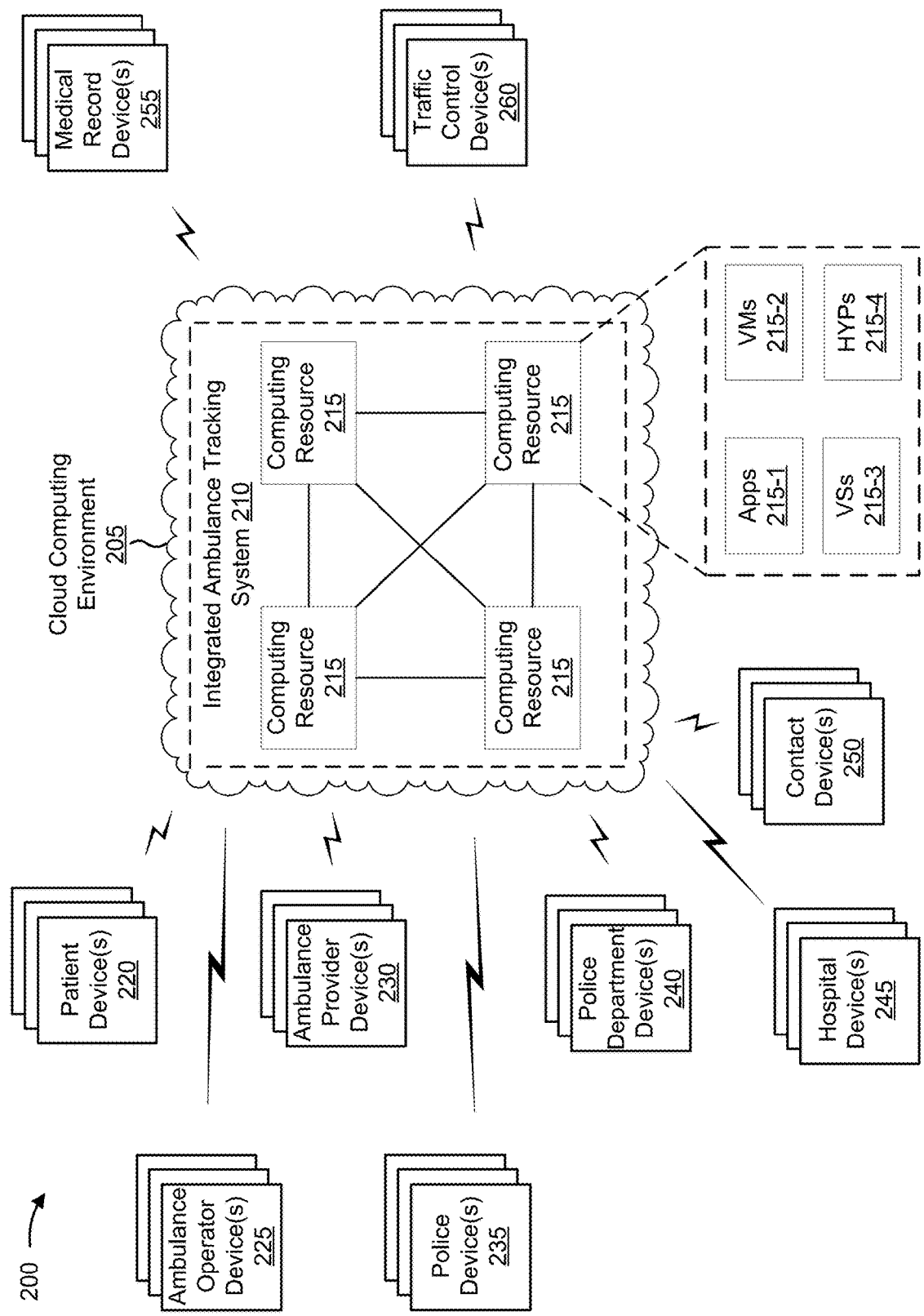
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a cloud computing environment 205, an integrated ambulance tracking system 210, a set of computing resources 215, a set of patient devices 220, a set of ambulance operator devices 225, a set of ambulance provider devices 230, a set of police devices 235, a set of police department devices 240, a set of hospital devices 245, a set of contact devices 250, a set of medical record devices 255, and a set of traffic control devices 260. Devices of environment 200 may interconnect via wired connections, wireless connections, or a combination of wired and wireless connections.

Cloud computing environment 205 includes an environment that hosts integrated ambulance tracking system 210. Cloud computing environment 205 may provide computation, software, data access, storage, etc. services that do not require end-user knowledge of a physical location and configuration of system(s) and/or device(s) that host integrated ambulance tracking system 210. As shown, cloud computing environment 205 may include a group of computing resources 215 (referred to collectively as "computing resources 215" and individually as "computing resource 215").

Computing resource 215 includes one or more personal computers, workstation computers, server devices, or another type of computation and/or communication device. In some implementations, computing resource 215 may host integrated ambulance tracking system 210. The cloud resources may include compute instances executing in computing resource 215, storage devices provided in computing resource 215, data transfer devices provided by computing resource 215, etc. In some implementations, computing resource 215 may communicate with other computing resources 215 via wired connections, wireless connections, or a combination of wired and wireless connections.

As further shown in FIG. 2, computing resource 215 includes a group of cloud resources, such as one or more applications ("APPs") 215-1, one or more virtual machines ("VMs") 215-2, one or more virtualized storages ("VSs") 215-3, or one or more hypervisors ("HYPs") 215-4.

Application 215-1 includes one or more software applications that may be provided to or accessed by one or more devices of environment 200. Application 215-1 may eliminate a need to install and execute the software applications on devices of environment 200. For example, application 215-1 may include software associated with integrated ambulance tracking system 210 and/or any other software capable of being provided via cloud computing environment 205. In some implementations, one application 215-1 may send/receive information to/from one or more other applications 215-1, via virtual machine 215-2.

Virtual machine 215-2 includes a software implementation of a machine (e.g., a computer) that executes programs like a physical machine. Virtual machine 215-2 may be either a system virtual machine or a process virtual machine, depending upon use and degree of correspondence to any real machine by virtual machine 215-2. A system virtual machine may provide a complete system platform that supports execution of a complete operating system ("OS"). A process virtual machine may execute a single program, and may support a single process. In some implementations, virtual machine 215-2 may execute on behalf of a user (e.g., associated with one or more devices of environment 200), and may manage infrastructure of cloud computing environment 205, such as data management, synchronization, or long-duration data transfers.

Virtualized storage 215-3 includes one or more storage systems and/or one or more devices that use virtualization techniques within the storage systems or devices of computing resource 215. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 215-4 may provide hardware virtualization techniques that allow multiple operating systems (e.g., "guest operating systems") to execute concurrently on a host computer, such as computing resource 215. Hypervisor 215-4 may present a virtual operating platform to the guest operating systems, and may manage the execution of the guest operating systems. Multiple instances of a variety of operating systems may share virtualized hardware resources.

Patient device 220 includes one or more devices associated with a patient. For example, patient device 220 may include a communication and/or computing device, such as a mobile device (e.g., a smart phone, a radiotelephone, a tablet computer, etc.), a laptop computer, a GPS device, a wearable communication device (e.g., a smart wristwatch, a pair of smart eyeglasses, etc.), or a similar type of device.

Ambulance operator device 225 includes one or more devices associated with an ambulance operator (e.g., an ambulance driver or an emergency medical technician). For example, ambulance operator device 225 may include a communication and/or computing device, such as a mobile device (e.g., a smart phone, a radiotelephone, a tablet computer, etc.), a laptop computer, a GPS device, a wearable communication device (e.g., a smart wristwatch, a pair of smart eyeglasses, etc.), or a similar type of device. In some implementations, ambulance operator device 225 may be integrated into a vehicle, such as an ambulance. For example, ambulance operator device 225 may be integrated into a communication and/or computing system (e.g., a dashboard system) of an ambulance. In some implementations, an ambulance may be a motor vehicle that is driven on roads, such as a truck, a van, a car, and/or the like. In some implementations, an ambulance may be an aircraft, such as a helicopter, an airplane, and/or the like. Additionally, or alternatively, an ambulance may be an unamend aerial vehicle (UAV), such as a drone.

Ambulance provider device 230 includes one or more devices associated with an ambulance provider (e.g., emergency personnel that travels with an ambulance, is a passenger in the ambulance, etc.), such as an emergency medical technician. For example, ambulance provider device 230 may include a communication and/or computing device, such as a mobile device (e.g., a smart phone, a radiotelephone, a tablet computer, etc.), a laptop computer, a desktop computer, a GPS device, a wearable communication device (e.g., a smart wristwatch, a pair of smart eyeglasses, etc.), or a similar type of device. In some implementations, ambulance provider device 230 may be integrated into one or more communication and/or computing systems inside an ambulance (e.g., a rear section of an ambulance used to treat patients).

Police device 235 includes one or more devices associated with a police officer (e.g., a field officer, a patrol officer, etc.). For example, police device 235 may include a communication and/or computing device, such as a mobile device (e.g., a smart phone, a radiotelephone, a tablet computer, etc.), a laptop computer, a GPS device, a wearable communication device (e.g., a smart wristwatch, a pair of smart eyeglasses, etc.), or a similar type of device. In some implementations, police device 235 may be integrated into a vehicle, such as a police car. For example, police device 235 may be integrated into a communication and/or computing system (e.g., a dashboard system) of a police vehicle.

Police department device 240 includes one or more devices associated with a police department (e.g., a police headquarters). For example, police department device 240 may include a communication and/or computing device, such as a mobile device (e.g., a smart phone, a radiotelephone, a tablet computer, etc.), a laptop computer, a desktop computer, a GPS device, a wearable communication device (e.g., a smart wristwatch, a pair of smart eyeglasses, etc.), or a similar type of device. In some implementations, police department device 240 may be located within a police department building.

Hospital device 245 includes one or more devices associated with a hospital or other type of care facility (e.g., a clinic, an animal hospital, a veterinarian, etc.). For example, hospital device 245 may include a communication and/or computing device, such as a mobile device (e.g., a smart phone, a radiotelephone, a tablet computer, etc.), a laptop computer, a desktop computer, a GPS device, a wearable communication device (e.g., a smart wristwatch, a pair of smart eyeglasses, etc.), or a similar type of device. In some implementations, hospital device 245 may be located within a hospital building.

Contact device 250 includes one or more devices associated with a contact of a patient (e.g., a person designated as an emergency contact, a family member, a friend, a family doctor, or the like). For example, contact device 250 may include a communication and/or computing device, such as a mobile device (e.g., a smart phone, a radiotelephone, a tablet computer, etc.), a laptop computer, a desktop computer, a GPS device, a wearable communication device (e.g., a smart wristwatch, a pair of smart eyeglasses, etc.), or a similar type of device.

Medical record device 255 includes one or more devices capable of storing electronic medical records (EMR), electronic health records (EHR), and/or other information associated with a patient. For example, medical record device 255 may include a server device, which may be hosted in a cloud computing environment and/or a data center. Integrated ambulance tracking system 210 may communicate with medical record device 255 to obtain such information in relation to providing an ambulance coordination service.

Traffic control device 260 includes one or more devices capable of controlling a set of traffic signals. For example, traffic control device 260 may include a traffic signal, a controller associated with a traffic signal, a sensor associated with a traffic signal, or the like. Integrated ambulance tracking system 210 may communicate with one or more traffic control devices 260 to control traffic signals associated with a route of an ambulance.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
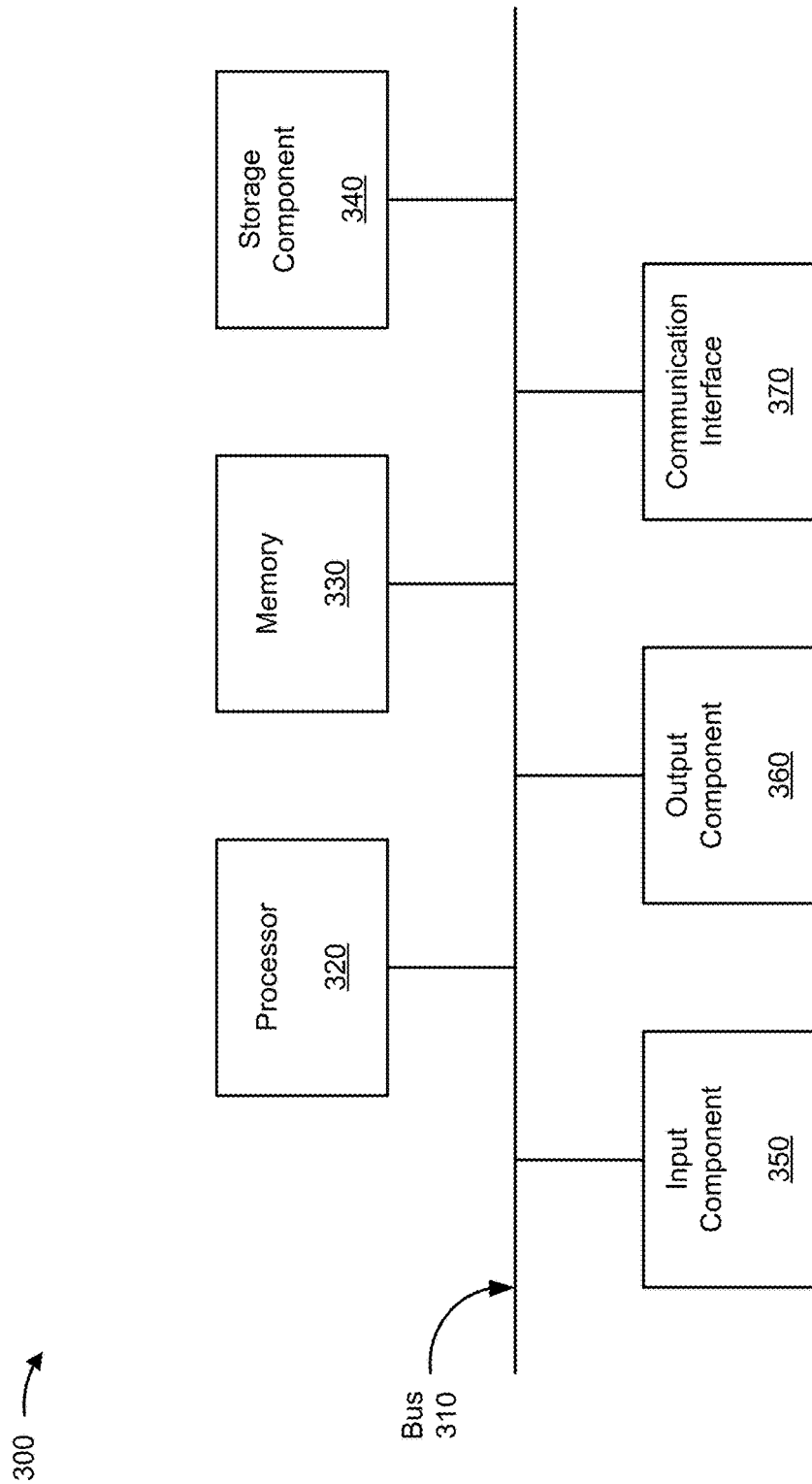
FIG. 3 is a diagram of example components of one or more devices of FIG. 2.

FIG. 3 is a diagram of example components of a device 300. Device 300 may correspond to integrated ambulance tracking system 210, computing resource 215, patient device 220, ambulance operator device 225, ambulance provider device 230, police device 235, police department device 240, hospital device 245, contact device 250, medical record device 255, and/or traffic control device 260. In some implementations, integrated ambulance tracking system 210, computing resource 215, patient device 220, ambulance operator device 225, ambulance provider device 230, police device 235, police department device 240, hospital device 245, contact device 250, medical record device 255, and/or traffic control device 260 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a processor (e.g., a central processing unit (CPU), a graphics processing unit (GPU), and/or an accelerated processing unit (APU)), a microprocessor, a microcontroller, and/or any processing component (e.g., a field-programmable gate array (FPGA) and/or an application-specific integrated circuit (ASIC)) that interprets and/or executes instructions. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
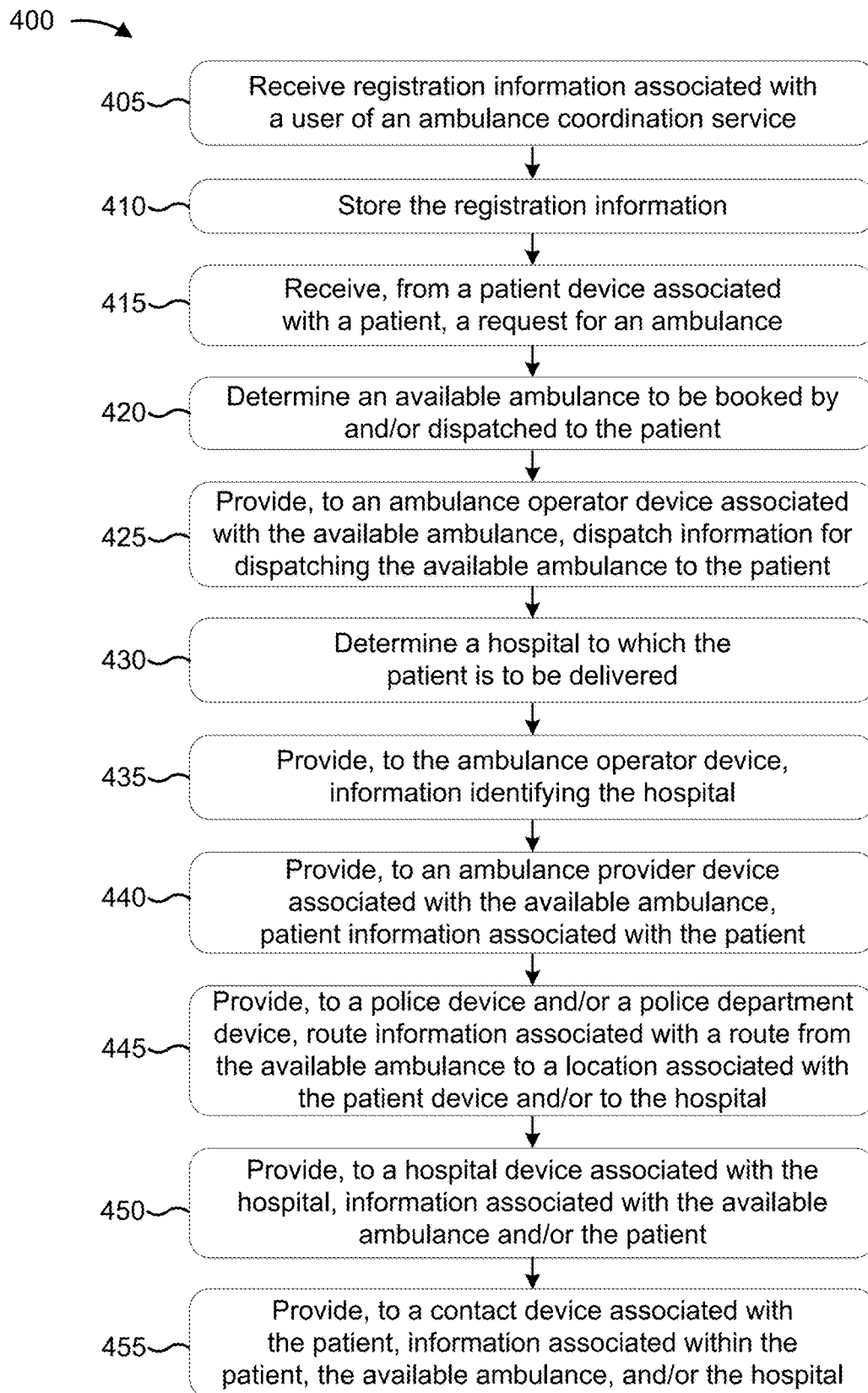
FIG. 4 is a flow chart of an example process for providing an ambulance coordination service.

FIG. 4 is a flow chart of an example process 400 for providing an ambulance coordination service. In some implementations, one or more process blocks of FIG. 4 may be performed by integrated ambulance tracking system 210. In some implementations, one or more process blocks of FIG. 4 may be performed by another device or a group of devices separate from or including integrated ambulance tracking system 210, such as computing resource 215, patient device 220, ambulance operator device 225, ambulance provider device 230, police device 235, police department device 240, hospital device 245, contact device 250, medical record device 255, and/or traffic control device 260.

As shown in FIG. 4, process 400 may include receiving registration information associated with a user of an ambulance coordination service (block 405). For example, integrated ambulance tracking system 210 may receive registration information. The registration information may include information associated with registering a user for an ambulance coordination service provided by integrated ambulance tracking system 210. The user may be associated with a role, such as a patient, an ambulance operator, an ambulance provider, a police officer, a police department user, a hospital user, and/or a contact person. In some implementations, a user may have more than one role, and integrated ambulance tracking system 210 may receive registration information for each role of the user.

In some implementations, different roles may be associated with different registration information, and integrated ambulance tracking system 210 may request registration information based on a role of the user. For example, registration information associated with a patient may be referred to as patient information, registration information associated with an ambulance operator may be referred to as ambulance operator information, registration information associated with an ambulance provider may be referred to as ambulance provider information, registration information associated with a police officer may be referred to as police officer information, registration information associated with a police department user may be referred to as police department information, registration information associated with a hospital user may be referred to as hospital information, and registration information associated with a contact person may be referred to as contact information.

In some implementations, integrated ambulance tracking system 210 may obtain the registration information based on user input (e.g., provided by at least one of patient device 220, ambulance operator device 225, ambulance provider device 230, police device 235, police department device 240, hospital device 245, contact device 250). Additionally, or alternatively, integrated ambulance tracking system 210 may obtain the information by accessing a data structure (e.g., a database stored by medical record device 255).

Example user interfaces and example operations associated with inputting registration information are described below in connection with FIGS. 5-14.

As further shown in FIG. 4, process 400 may include storing the registration information (block 410). For example, integrated ambulance tracking system 210 may store the registration information, in association with the user, for later use in connection with an ambulance coordination service provided by integrated ambulance tracking system 210. In some implementations, integrated ambulance tracking system 210 may store the registration information in one or more memory devices local to integrated ambulance tracking system 210. In some implementations, integrated ambulance tracking system 210 may store the registration information in one or more memory devices remote from integrated ambulance tracking system 210. In some implementations, integrated ambulance tracking system 210 may store some of the registration information in one or more memory devices local to integrated ambulance tracking system 210 and may store some of the registration information in one or more memory devices remote from integrated ambulance tracking system 210.

As further shown in FIG. 4, process 400 may include receiving, from a patient device associated with a patient, a request for an ambulance (block 415), and determining an available ambulance to be booked by and/or dispatched to the patient (block 420). For example, a patient may interact with patient device 220 to request an ambulance (e.g., for a user directly interacting with patient device 220 or for another person, such as a person in the vicinity of patient device 220). In some implementations, the patient may interact with patient device 220 to input a medical situation associated with the request (e.g., heart attack, stroke, car accident, severed finger, or another type of injury).

In some implementations, the patient may indicate that the patient needs an ambulance, and integrated ambulance tracking system 210 may identify an available ambulance to be dispatched to the patient, as described below. Additionally, or alternatively, integrated ambulance tracking system 210 may provide, to patient device 220, information that identifies a set of available ambulances, and patient device 220 may output this information (e.g., on a map). In this case, the patient may interact with patient device 220 to select an ambulance to be dispatched to the patient.

As an example, integrated ambulance tracking system 210 may determine an available ambulance (e.g., a single ambulance), of a set of ambulances, to be dispatched to the patient (e.g., reserved and/or booked by the patient). In some implementations, integrated ambulance tracking system 210 may determine the available ambulance based on a location associated with patient device 220 (e.g., a closest geographic proximity of an ambulance to the location, a fastest travel time of an ambulance to the location, or the like), based on patient selection of an ambulance (e.g., via a user interface of patient device 220), based on ambulance operator input (e.g., indicating a confirmation that the ambulance operator is available to pick up the patient), based on a hospital operator input (e.g., indicating that the hospital is equipped or prepared to handle the medical situation of the patient), based on traffic conditions associated with a route to the patient, or the like. In some implementations, integrated ambulance tracking system 210 may generate a score for each available ambulance (e.g., based on one or more of the factors identified above) within a threshold distance of patient device 220 and may select an ambulance, of the available ambulances, based on the scores of the available ambulances.

In some implementations, integrated ambulance tracking system 210 may use data analytics to predict the occurrence of a medical situation in a location, and may transmit a message to an ambulance operator device 225 to instruct an ambulance operator to drive the ambulance to the location or within a proximity of the location. For example, integrated ambulance tracking system 210 may use GPS data associated with patient devices 220 to determine that a threshold number of people are located in a location, and may transmit a message to ambulance operator device 225 instructing an ambulance operator to drive to the location in anticipation of a medical situation occurring in the location.

As another example, integrated ambulance tracking system 210 may use data regarding previous requests for ambulances to predict a time and/or location for future requests, and may transmit a message to ambulance operator device 225 instructing an ambulance operator to drive to be in a predicted location at a predicted time in anticipation of a medical situation occurring in the location. In some implementations, integrated ambulance tracking system 210 may use machine learning to make such predictions (e.g., using data associated with previous requests for ambulances to train a machine learning model).

Example user interfaces and example operations associated with requesting, booking, and dispatching an ambulance are described below in connection with FIGS. 15-22.

As further shown in FIG. 4, process 400 may include providing, to an ambulance operator device associated with the available ambulance, dispatch information for dispatching the available ambulance to the patient (block 425). For example, integrated ambulance tracking system 210 may provide, to ambulance operator device 225, dispatch information. The dispatch information may identify a fastest route to the patient and/or patient device 220, in some implementations. Additionally, or alternatively, the dispatch information may include patient information associated with the patient (e.g., a medical situation indicated by the patient, electronic medical records associated with the patient, registration information associated with the patient, or the like). An example user interface associated with providing dispatch information to ambulance operator device 225 is described below in connection with FIG. 23.

As further shown in FIG. 4, process 400 may include determining a hospital to which the patient is to be delivered (block 430). For example, integrated ambulance tracking system 210 may determine a hospital based on a location of the hospital, patient device 220, and/or the ambulance (e.g., as indicated by ambulance operator device 225). Additionally, or alternatively, integrated ambulance tracking system 210 may determine a hospital based on a medical situation associated with the patient, registration information associated with the patient, patient information associated with the patient, a preference indicated by the patient, traffic conditions associated with a route to the hospital (e.g., the closest hospital geographically may be different from the hospital with that can be driven to fastest), or the like. In some implementations, integrated ambulance tracking system 210 may generate a score for each hospital within a threshold distance of the patient (e.g., based on one or more of the factors identified above) and may select a hospital, of the possible hospitals, based on the scores of the possible hospitals.

As further shown in FIG. 4, process 400 may include providing, to the ambulance operator device, information identifying the hospital (block 435). For example, integrated ambulance tracking system 210 may provide, to ambulance operator device 225, information identifying the hospital determined by integrated ambulance tracking system 210. The information may identify a fastest route to the hospital, in some implementations. An example user interface associated with providing information, associated with the hospital, to ambulance operator device 225 is described below in connection with FIG. 24.

As further shown in FIG. 4, process 400 may include providing, to an ambulance provider device associated with the available ambulance, patient information associated with the patient (block 440). For example, integrated ambulance tracking system 210 may provide, to ambulance provider device 230, patient information associated with the patient. The patient information may include, for example, information input by the patient to patient device 220 (e.g., information identifying a medical situation), electronic medical records associated with the patient, registration information associated with the patient, or the like. In this way, an ambulance provider (e.g., an EMT) may be prepared with relevant information for treating the patient when the ambulance arrives to pick up the patient. Example user interfaces associated with providing patient information to ambulance provider device 230 are described below in connection with FIGS. 25-28.

As further shown in FIG. 4, process 400 may include providing, to a police device and/or a police department device, route information associated with a route from the available ambulance to a location associated with the patient device and/or to the hospital (block 445). For example, integrated ambulance tracking system 210 may provide, to police device 235 and/or police department device 240, route information associated with the available ambulance. For example, the route information may identify a route from the ambulance to the patient, a route from the ambulance to the hospital, or the like. In this way, police personnel can assist with clearing the route of traffic. In some implementations, integrated ambulance tracking system 210 may identify police devices 235 and/or police department devices 240 within a geographic proximity of the route(s), and may send the route information to those police devices 235 and/or police department devices 240. This conserves network resources as compared to providing the route information to more police devices 235 and/or police department devices 240 than necessary. Example user interfaces associated with providing route information to police device 235 and/or police department device 240 are described below in connection with FIGS. 29-30.

Figure 28:
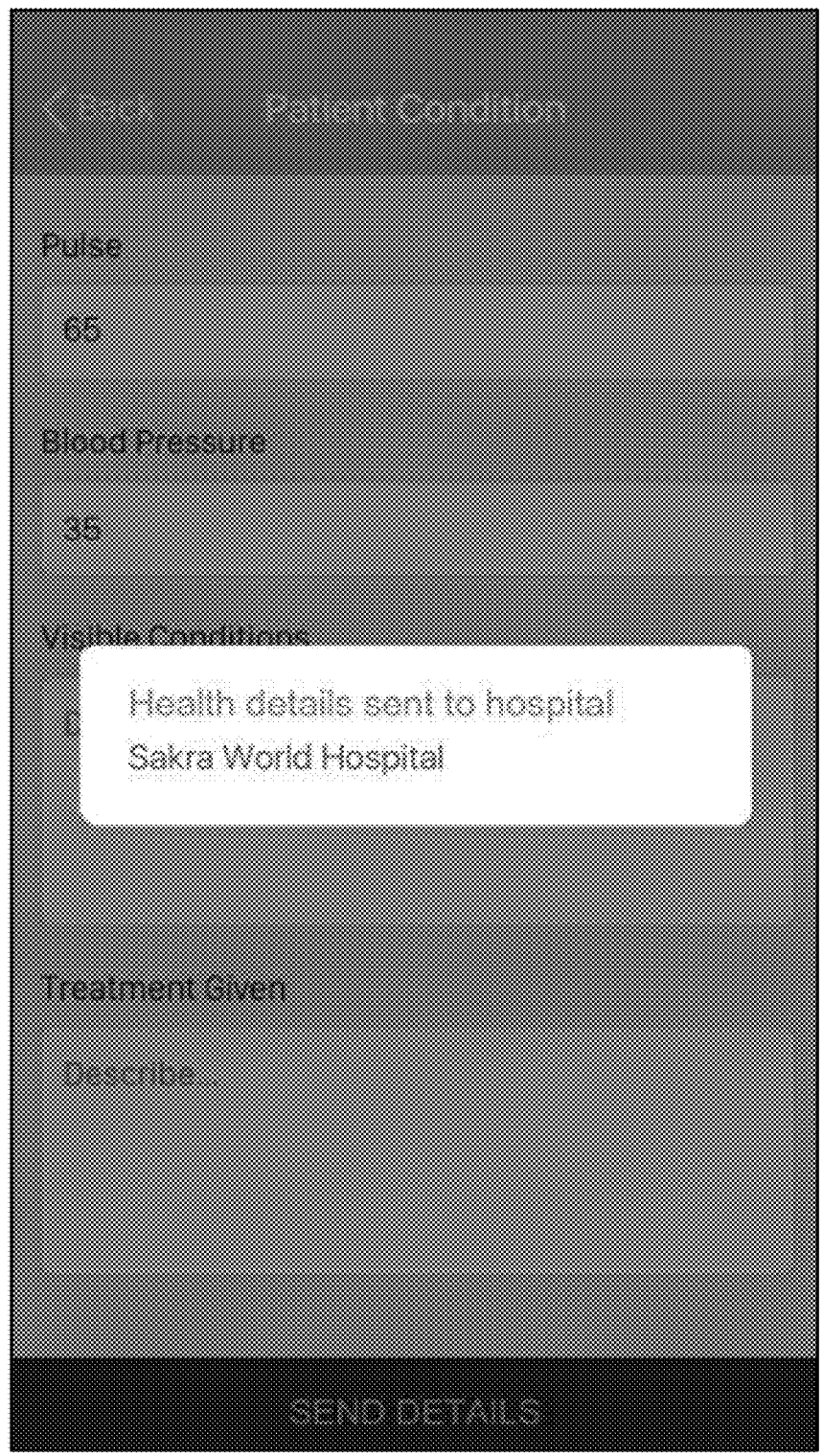

As further shown in FIG. 4, process 400 may include providing, to a hospital device associated with the hospital, information associated with the available ambulance and/or the patient (block 450). For example, integrated ambulance tracking system 210 may provide ambulance information and/or patient information to hospital device 245 associated with a hospital for which the available ambulance is destined. For example, integrated ambulance tracking system 210 may provide a notification that the ambulance will be coming to the hospital, an indication of an estimated time of the ambulance's arrival (e.g., an estimated arrival time), information regarding the patient (e.g., based on electronic medical records, information input to the ambulance provider device, information input to the patient device, patient information, registration information, insurance information, etc.), or the like. In this way, integrated ambulance tracking system 210 assists hospital staff with preparing appropriate equipment based on a medical situation associated with the patient. In some implementations, integrated ambulance tracking system may receive information from ambulance provider device 230, and may provide the information to hospital device 245, as shown in FIG. 28.

Additionally, or alternatively, integrated ambulance tracking system 210 may provide insurance information to an insurance provider device associated with an insurance carrier of the patient. In this way, insurance payments can be coordinated to the ambulance operator, the hospital, and/or the like.

As further shown in FIG. 4, process 400 may include providing, to a contact device associated with the patient, information associated with the patient, the available ambulance, and/or the hospital (block 455). For example, integrated ambulance tracking system 210 may provide notifications to one or more contact devices 250 associated with a family member of the patient, a friend of the patient, a doctor of the patient, or another contact of the patient. Such notifications may indicate a medical situation associated with the patient, a location of the patient (e.g., based on a location of patient device 220 and/or ambulance operator device 225), a hospital where the patient is being or has been taken, or the like. In some implementations, contact information for contact devices 250 may be included in registration information and/or electronic medical/health records associated with the patient. In this way, integrated ambulance tracking system 210 ensures efficient communication among all parties associated with the patient, and efficient use of network resources.

While implementations are described herein with respect to an integrated ambulance tracking system that coordinates messages sent between devices to facilitate swift pick up of a patient by an ambulance (e.g., an available ambulance), and swift delivery to a hospital, other implementations are possible. For example, an integrated vehicle tracking system may coordinate messages sent between devices to facilitate swift pick up of a user by a vehicle (e.g., an available vehicle), and swift delivery to a destination, in a similar manner as described herein.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIGS. 5-30 are diagrams of example user interfaces 500-3000 used in association with integrated ambulance tracking system 210. User interfaces 500-3000 may be provided for display by appropriate user devices 220-250.

Figure 5:
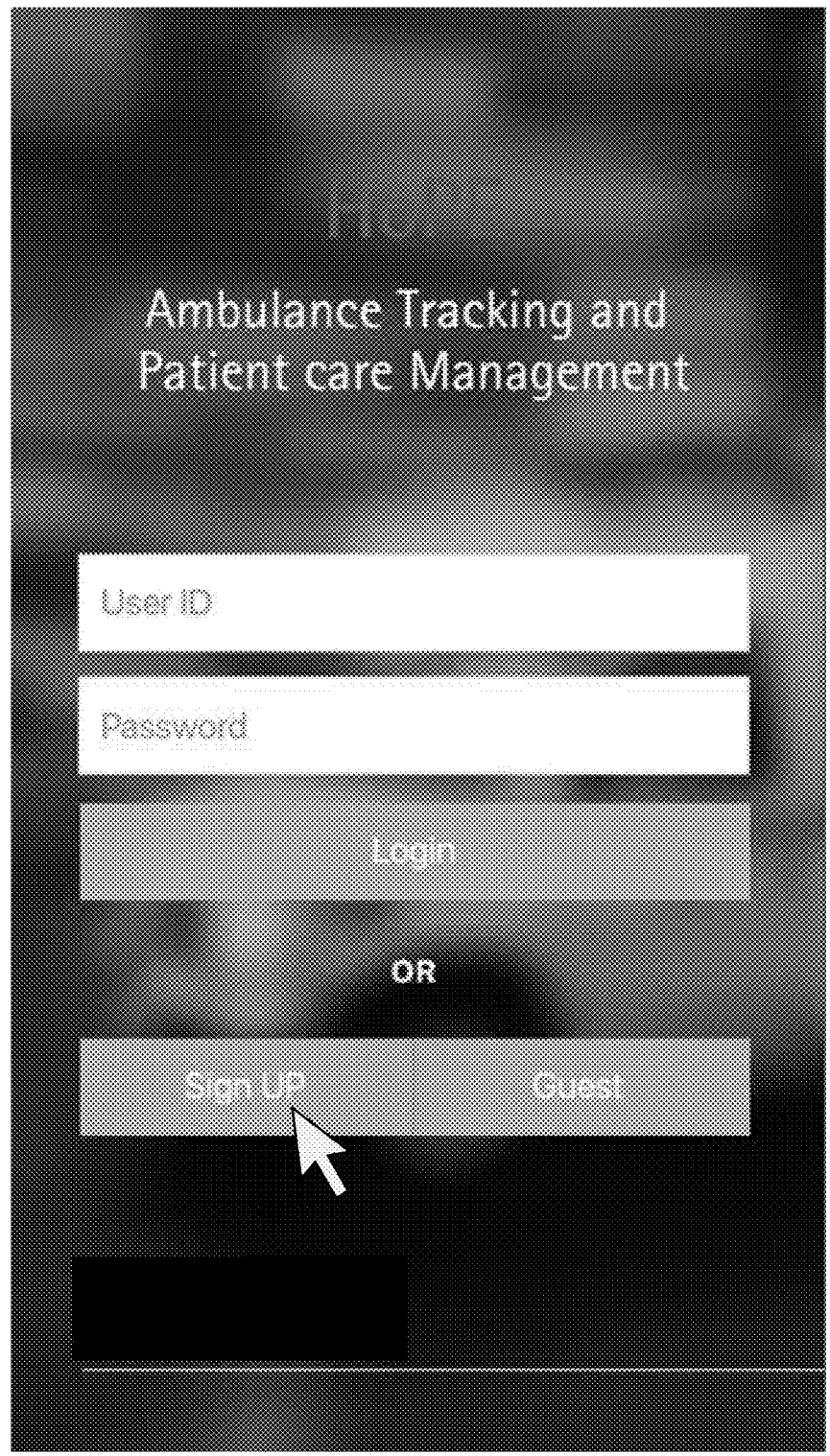
Figure 6:
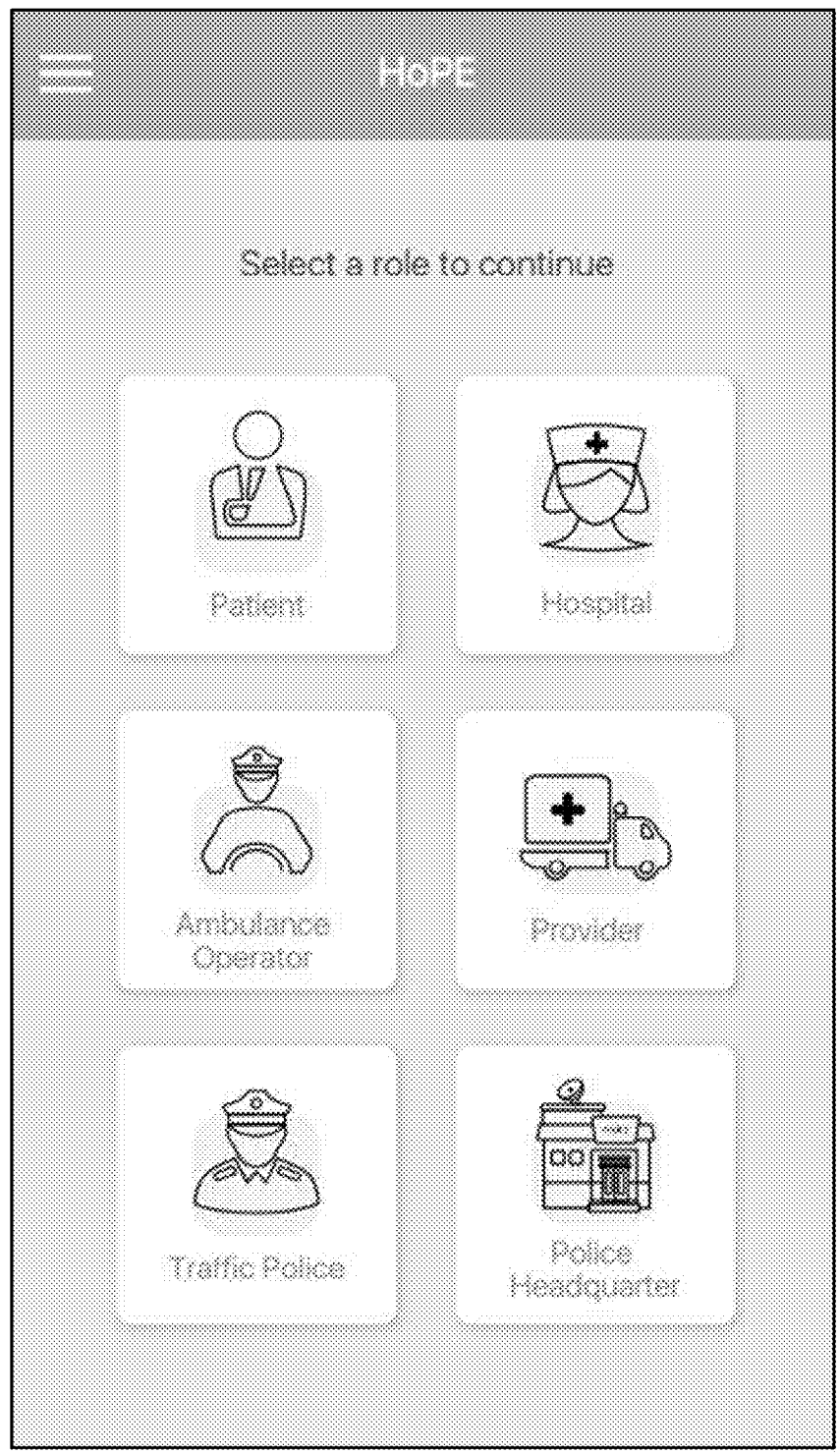

FIGS. 5 and 6 show example user interfaces and example operations associated with inputting registration information. For example, as shown in FIG. 5, a user may interact with a corresponding user device (e.g., one of user devices 220-250) to sign up for an ambulance coordination service using an ambulance coordination application (e.g., a web application or an application installed on the user device). As shown in FIG. 6, the user may interact with the user device to select a role of the user.

Figure 8:
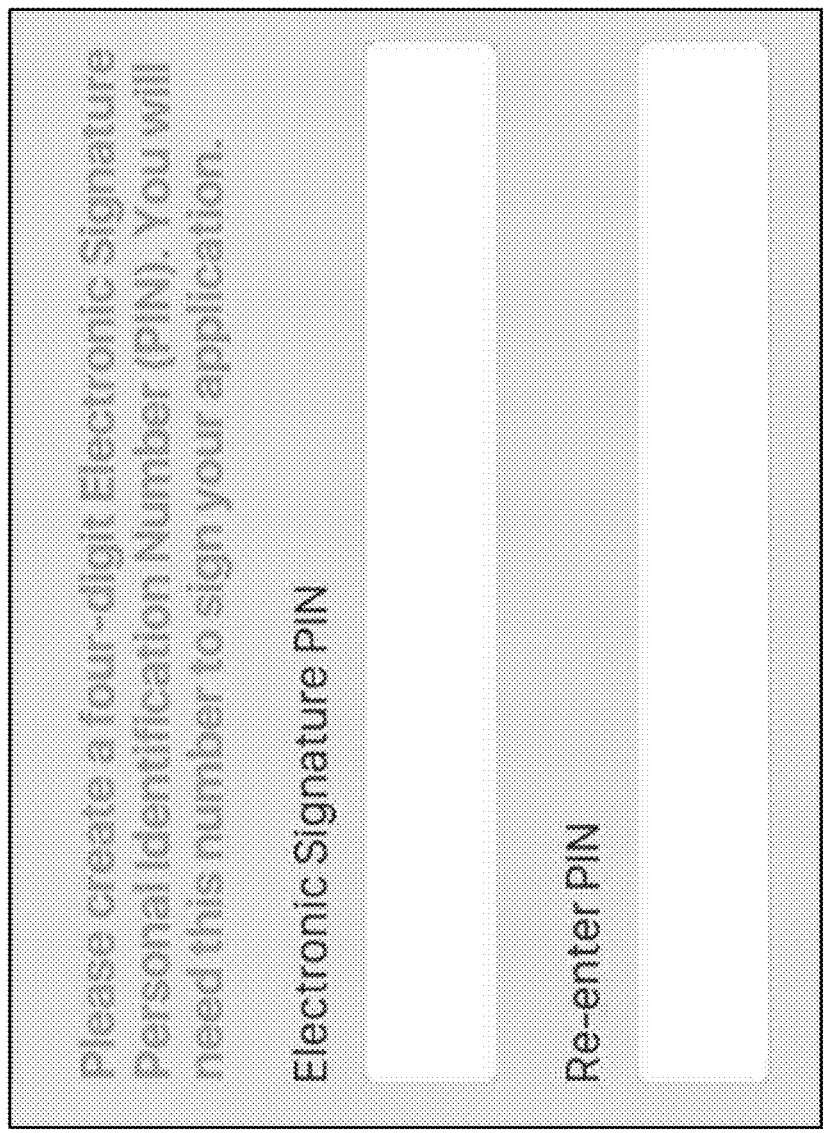
Figure 11:
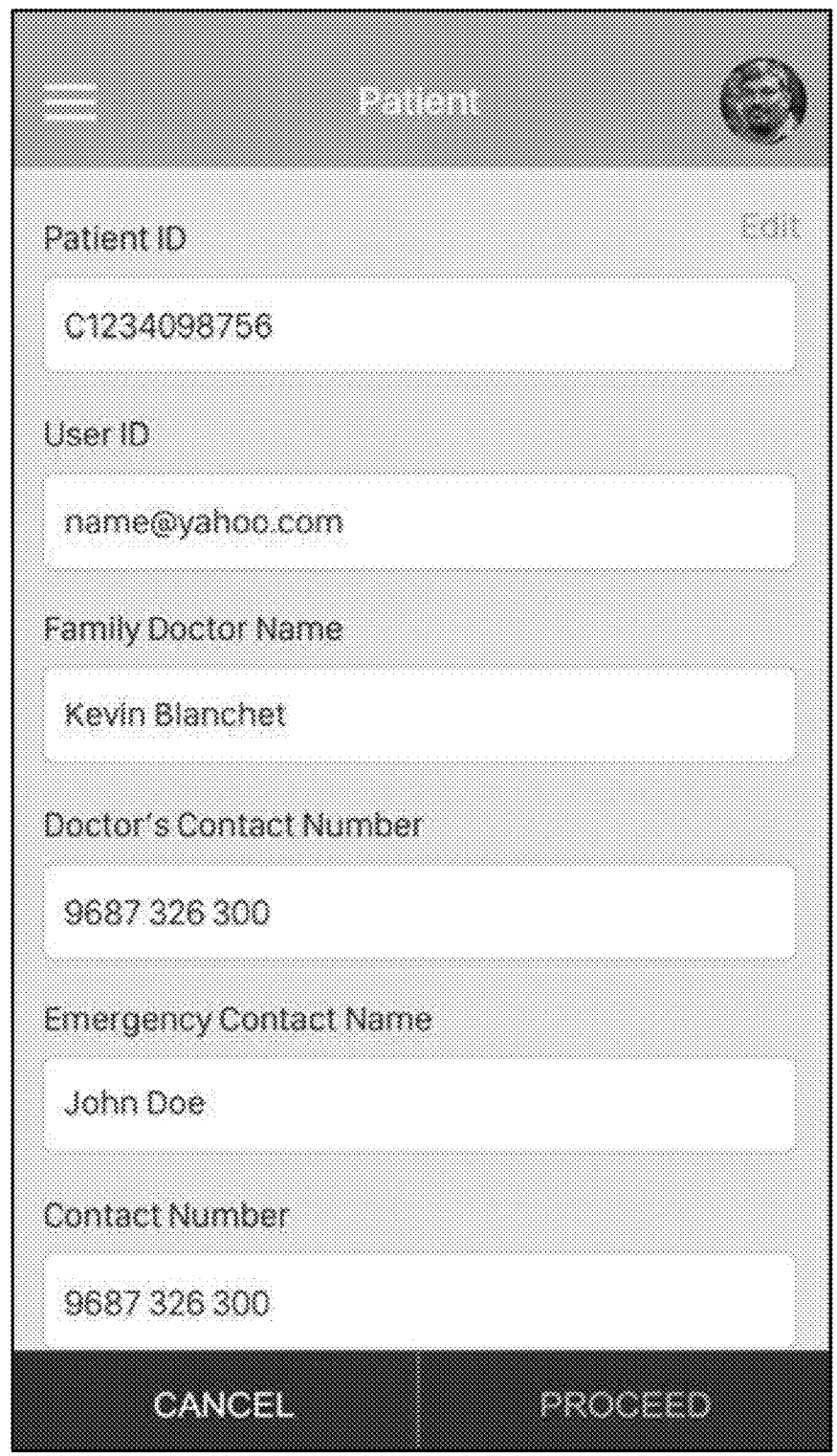

FIGS. 7-11 show examples of patient information that may be provided as registration information for a user identified as a patient. As shown in FIG. 7, a patient may input the patient's name, a patient identifier (e.g., an identifier used to obtain EHR or EMR), patient contact information (e.g., a phone number, an email address, a physical address, etc.), a user name for accessing the ambulance coordination application, and a password for accessing the ambulance coordination application. As shown in FIG. 8, the patient may input a personal identification number (PIN) to access the ambulance coordination application. As shown in FIG. 9, the patient may input contact information, such as contact information (e.g., a name, a phone number, an email address, etc.) of a family doctor, an emergency contact, or the like. As shown in FIG. 10, the patient may input medical information, such as information identifying allergies, information identifying health conditions, an EHR or EMR identifier (e.g., for accessing the patient's EHR or EMR), or the like. As shown in FIG. 11, the patient may verify the input information, and may interact with the user device to provide the patient information to integrated ambulance tracking system 210 (e.g., via a network).

Figure 12:
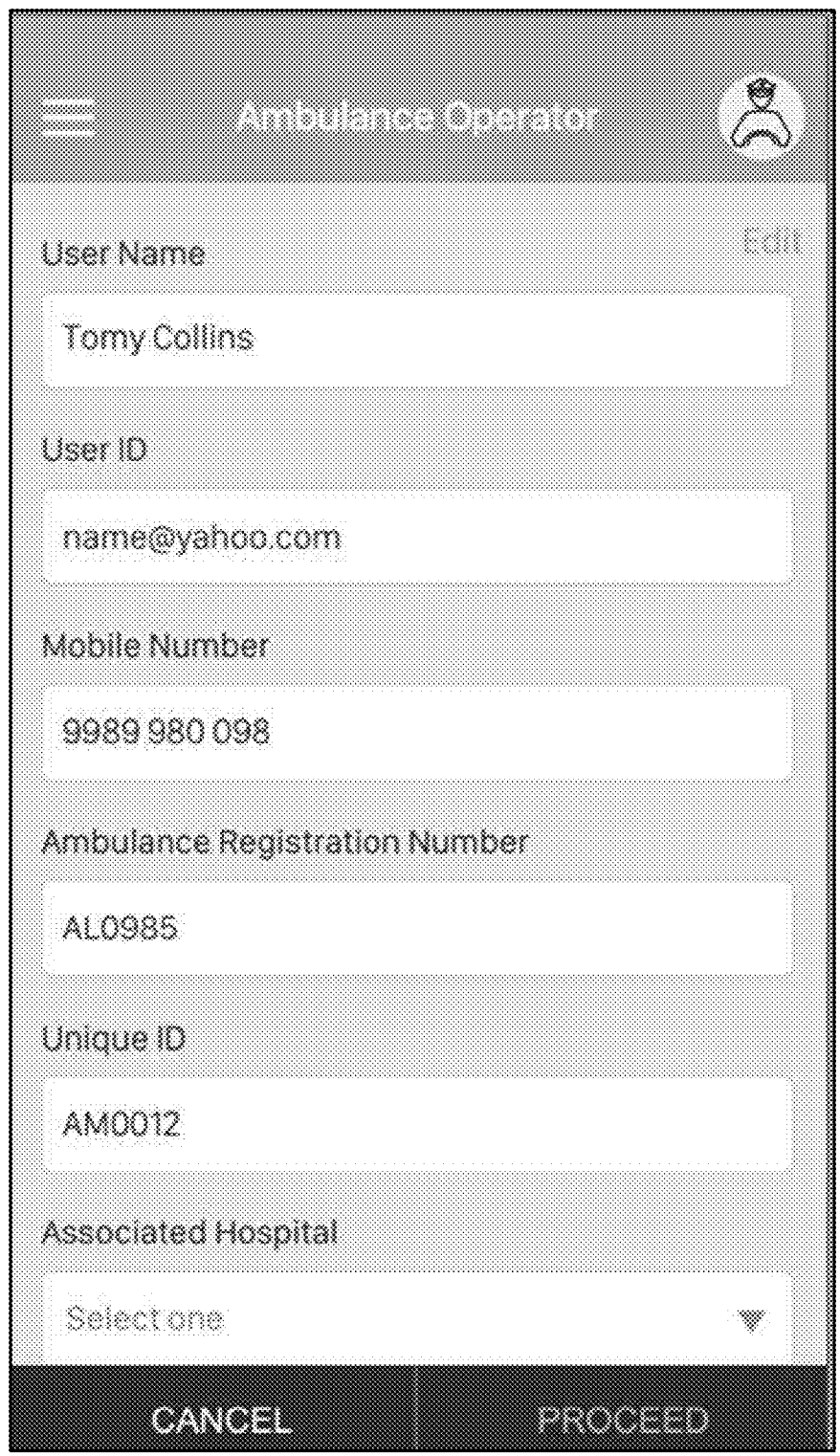

FIG. 12 shows an example of ambulance operator information that may be provided as registration information for a user identified as an ambulance operator. As shown in FIG. 12, an ambulance operator may input the ambulance operator's name, a user identifier, an email address, a phone number, an ambulance identifier (e.g., a registration number to identify an ambulance operated by the ambulance operator), an ambulance operator identifier (e.g., to uniquely identifier the ambulance operator), and/or information that identifies a hospital with which the ambulance or ambulance operator is associated.

In some implementations, an ambulance operator may drive different ambulances at different times, and may input multiple ambulance identifiers associated with the different ambulances. In this case, when the ambulance operator starts his or her shift and logs in to the ambulance coordination application, the user device may prompt the ambulance operator to select an ambulance identifier of the ambulance being driven by the ambulance operator. Additionally, or alternatively, a device of the ambulance may automatically communicate the ambulance identifier (e.g., via the user device) to integrated ambulance tracking system 210. In some implementations, integrated ambulance tracking system 210 may determine a location of the user device, may identify nearby hospitals (e.g., within a geographic proximity), and may provide information that identifies the nearby hospitals for selection by the ambulance operator as a hospital associated with the ambulance being driven by the ambulance operator.

Although not shown, similar registration information as described above for an ambulance operator may be input by an ambulance provider as ambulance provider information. For example, an ambulance provider may input the ambulance provider's name, a user identifier, an email address, a phone number, an ambulance identifier (e.g., a registration number to identify an ambulance in which the ambulance provider travels), an ambulance provider identifier (e.g., to uniquely identifier the ambulance provider), information that identifies a hospital with which the ambulance or ambulance provider is associated, information that identifies medical training of the ambulance provider (e.g., EMT, nurse, doctor, etc.), and/or information that identifies a medical specialty of the ambulance provider.

Figure 13:
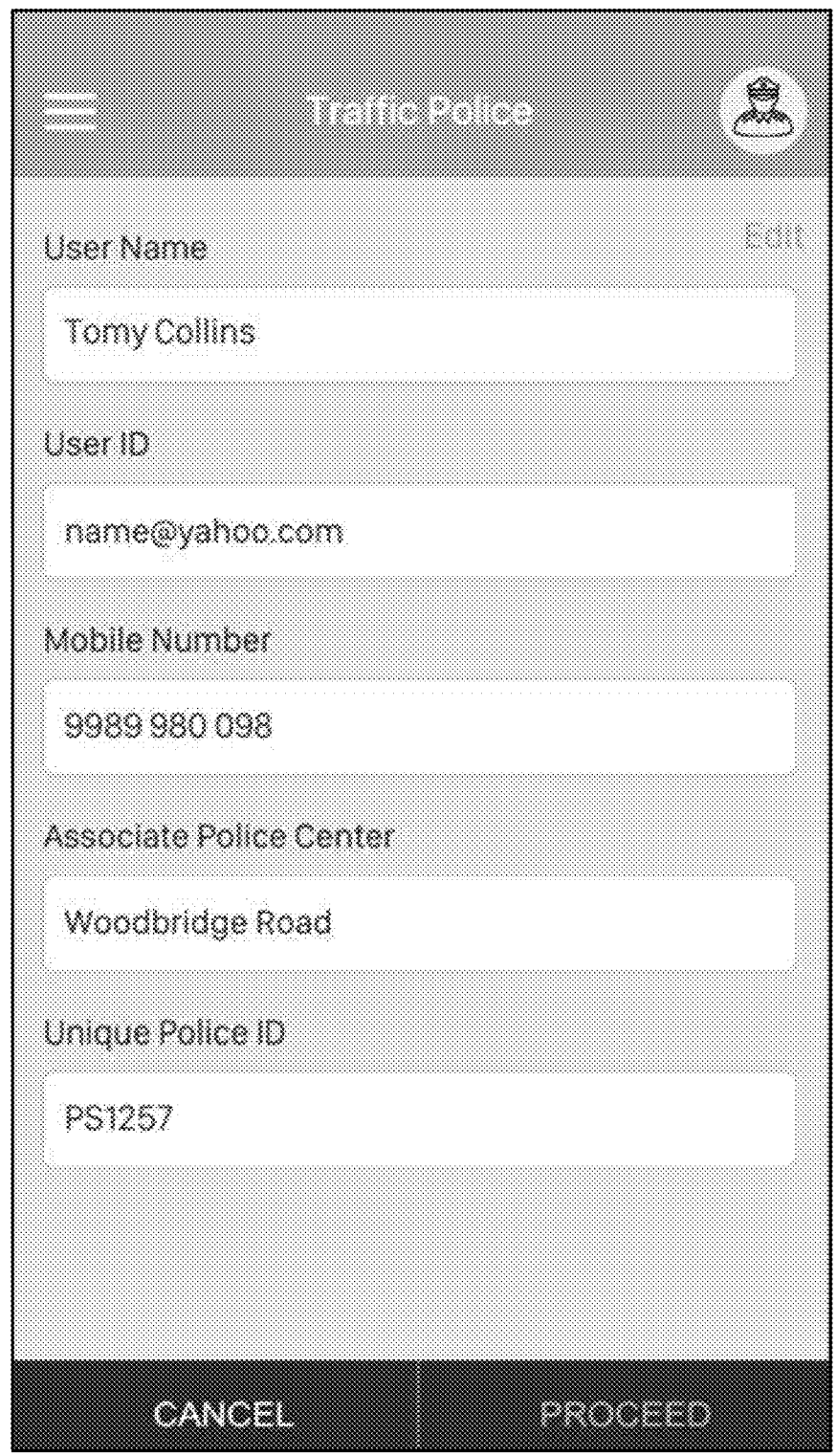

FIG. 13 shows an example of police officer information that may be provided as registration information for a user identified as a police officer. As shown in FIG. 13, a police officer may input the police officer's name, a user identifier, an email address, a phone number, information that identifies a police department with which the police officer is associated, a police vehicle identifier (e.g., a registration number to identify a police vehicle operated by the police operator), a police officer identifier (e.g., to uniquely identify the police officer), or the like. In some implementations, integrated ambulance tracking system 210 may determine a location of the user device, may identify nearby police departments (e.g., within a geographic proximity), and may provide information that identifies the nearby police departments for selection by the police officer as a police department associated with the police officer.

Figure 14:
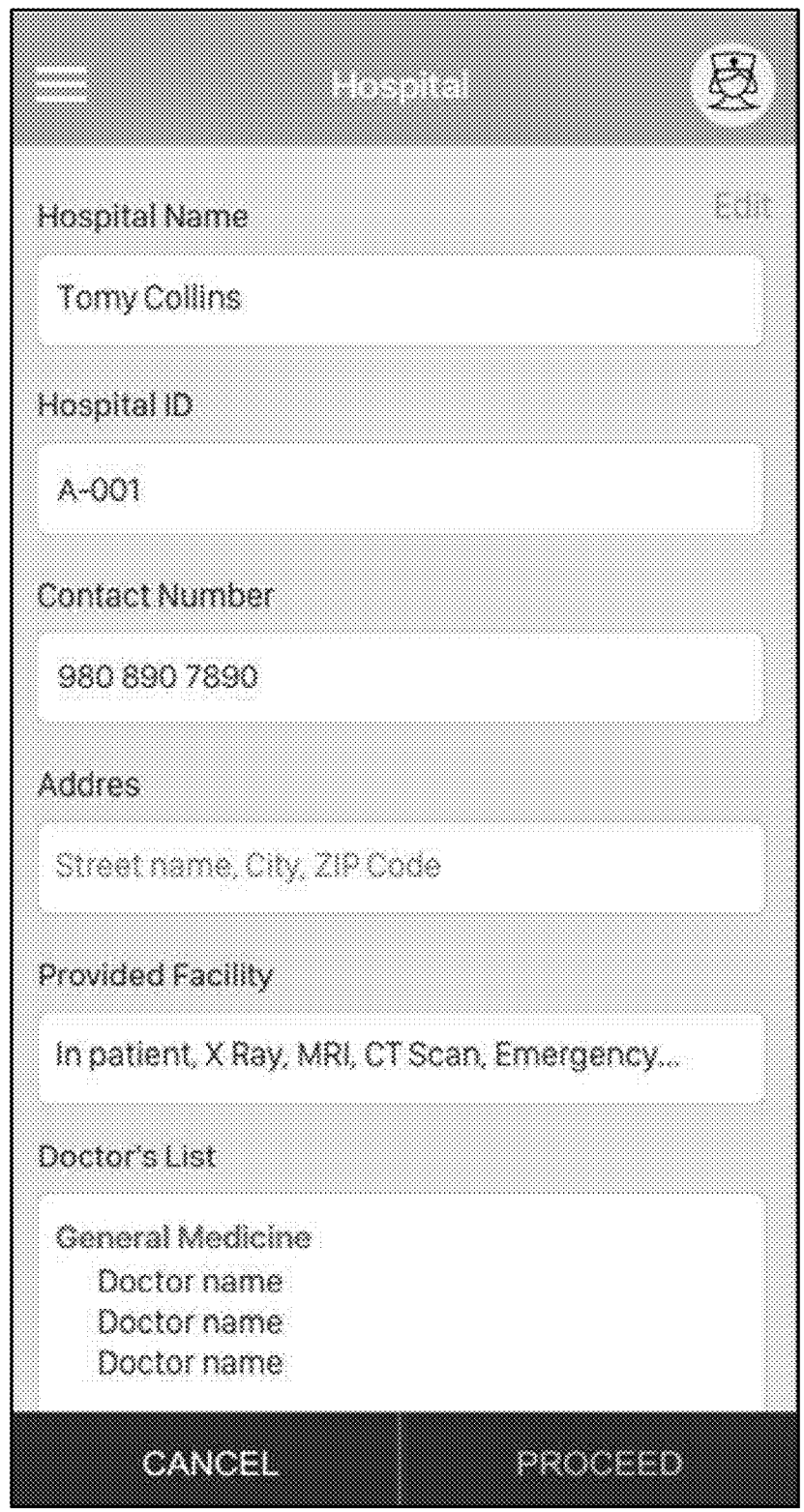

FIG. 14 shows an example of hospital information that may be provided as registration information for a user identified as a hospital user. As shown in FIG. 14, a hospital user may input the hospital user's name, a user identifier, an email address, a phone number, a name of the hospital, a hospital identifier (e.g., used to uniquely identify the hospital), a physical address of the hospital, services provided by the hospital and/or specialties of the hospital (e.g., in-patient care, x-rays, etc.), a list of doctors associated with the hospital, information that identifies specialties of the doctors (e.g., a type of medicine practiced by the doctor, such as general medicine, internal medicine, cardiology, neurology, etc.), or the like.

Although not shown, similar registration information as described above for a hospital user may be input by a police department user as police department information. For example, a police department user may input the police department user's name, a user identifier, an email address, a phone number, a name of the police department, a police department identifier (e.g., used to uniquely identify the police department), a physical address of the police department, a list of police officers associated with the police department, information that identifies specialties of the police officers (e.g., traffic police, homicide detective, etc.), or the like.

Figure 15:
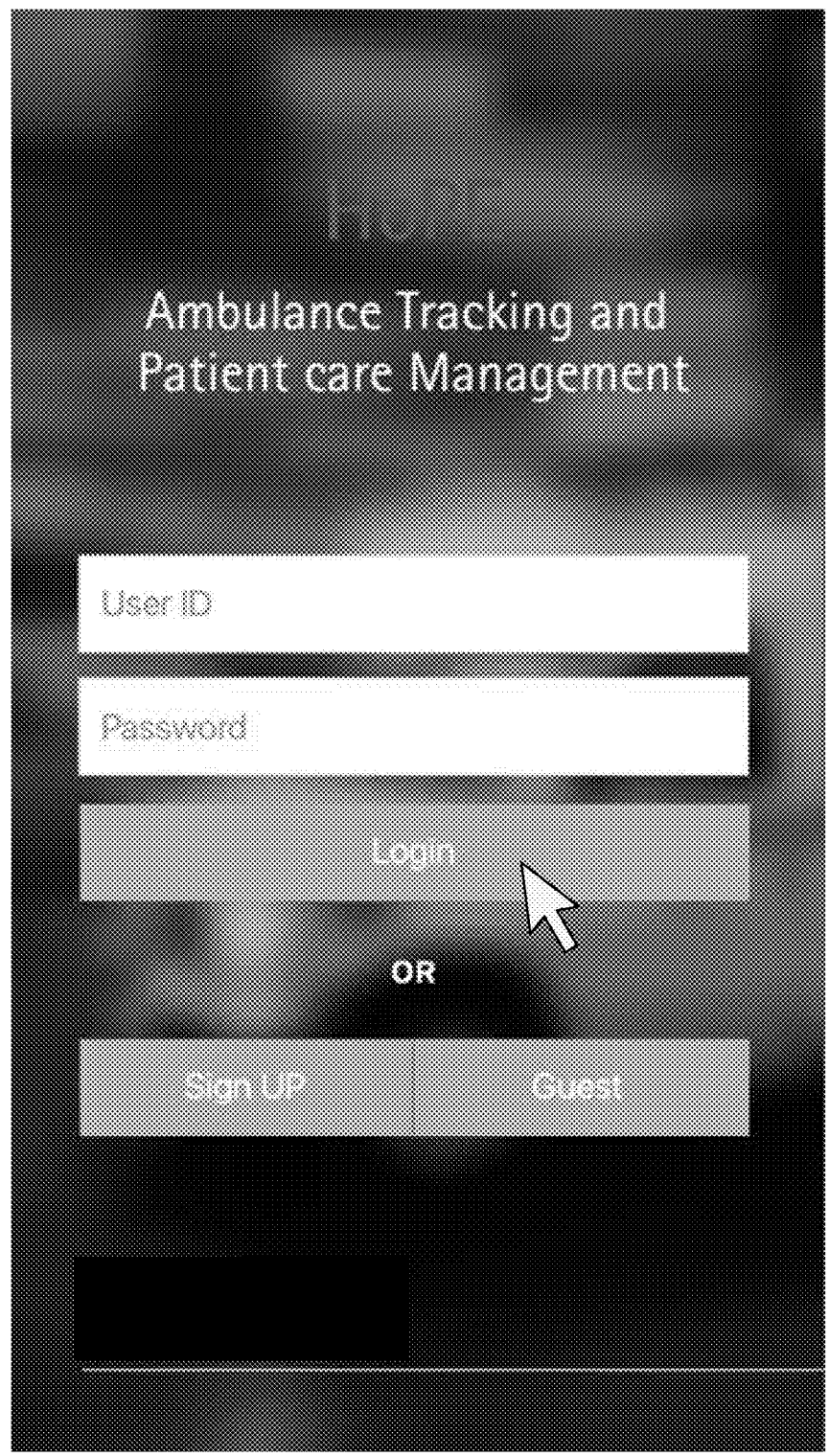
Figure 16:
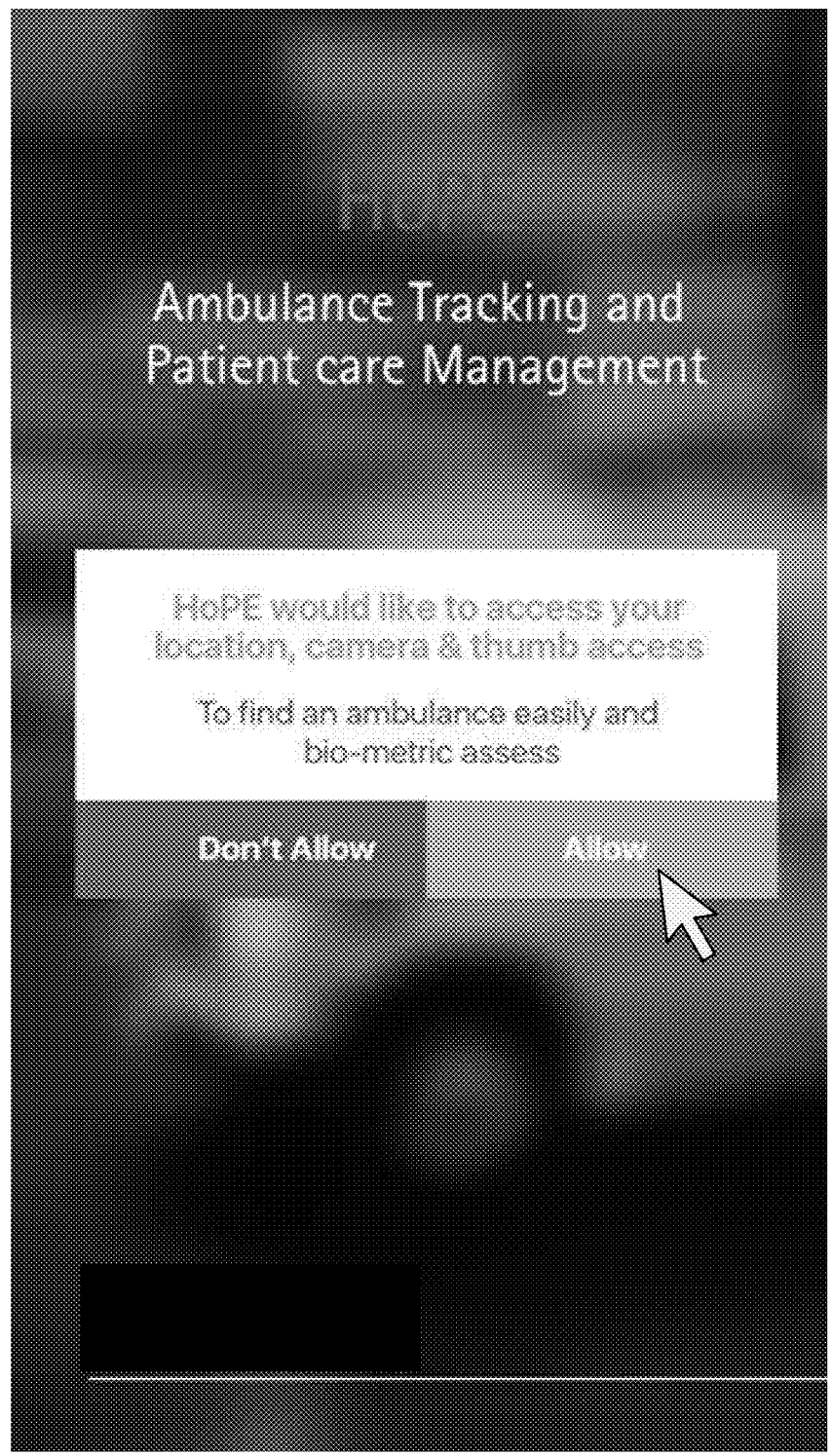

As shown in FIGS. 15 and 16, a patient may interact with patient device 220 to log in to an ambulance coordination application. In some implementations, the ambulance coordination application may use location services to identify a location of patient device 220. Additionally, or alternatively, the ambulance coordination application may use biometric information (e.g., a fingerprint, a thumbprint, facial recognition, a voice print, etc.) to authenticate and/or log in a patient.

Figure 17:
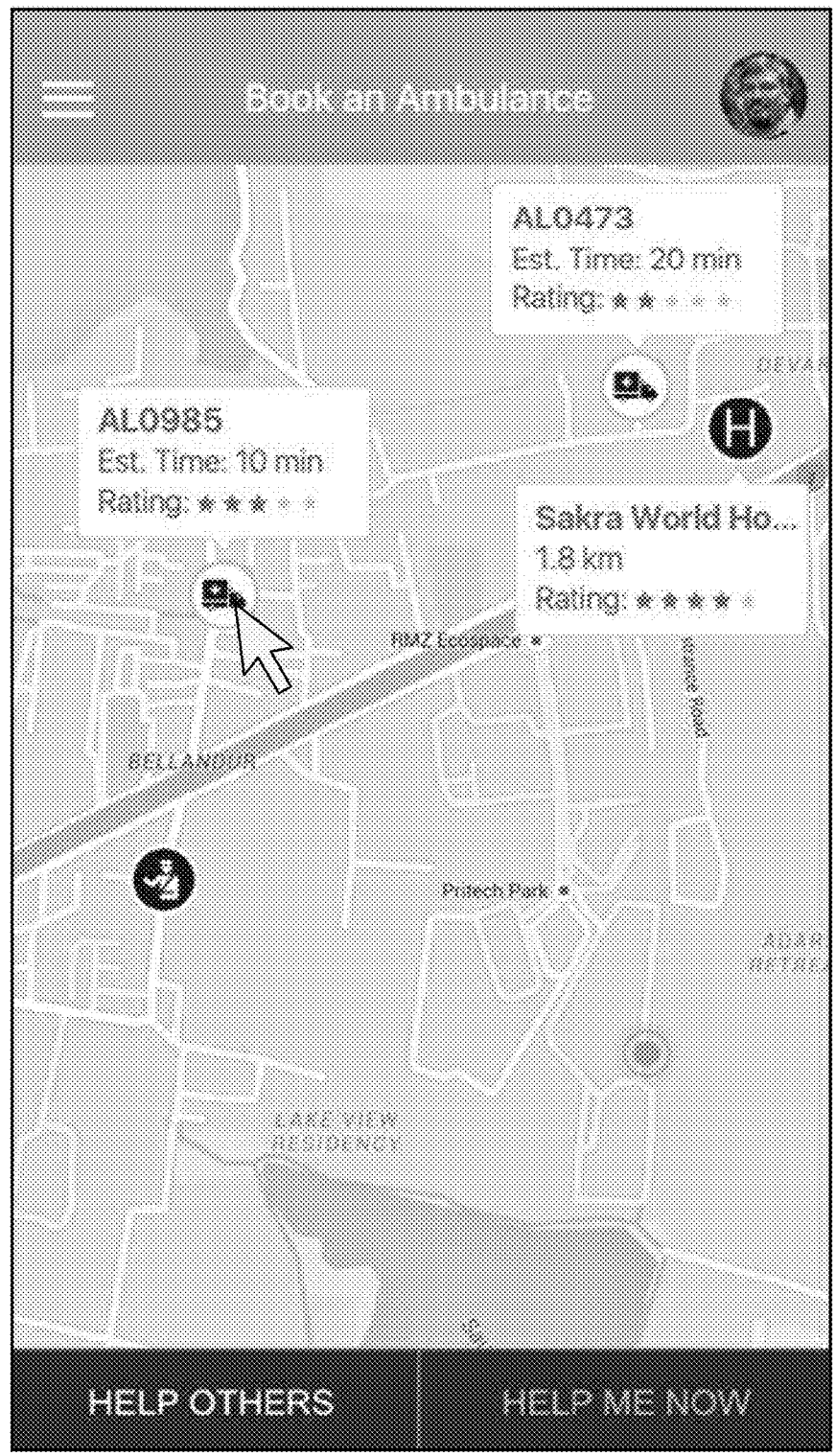

As shown in FIG. 17, integrated ambulance tracking system 210 may identify a set of ambulances and/or hospitals within a geographic proximity of patient device 220, and may provide information associated with the ambulances and/or hospitals to patient device 220. Patient device 220 may display a user interface with information associated with the ambulances and/or hospitals, such as an ambulance identifier, a hospital identifier (e.g., a hospital name), a geographic location of an ambulance or hospital on a map, an estimated travel time from an ambulance to patient device 220, a rating associated with an ambulance or hospital, or the like. In some implementations, the patient may interact with the user interface to select an ambulance to be dispatched to the patient. In some implementations, integrated ambulance tracking system 210 may automatically select an ambulance to be dispatched to the user. For example, integrated ambulance tracking system 210 may automatically select an ambulance based on a distance between the ambulances and patient device 220, based on a travel time from the ambulances to patient device 220, based on which ambulances are associated with a hospital closest to patient device 220 and/or a hospital that specializes in a medical condition indicated by the patient, or the like.

Figure 18:
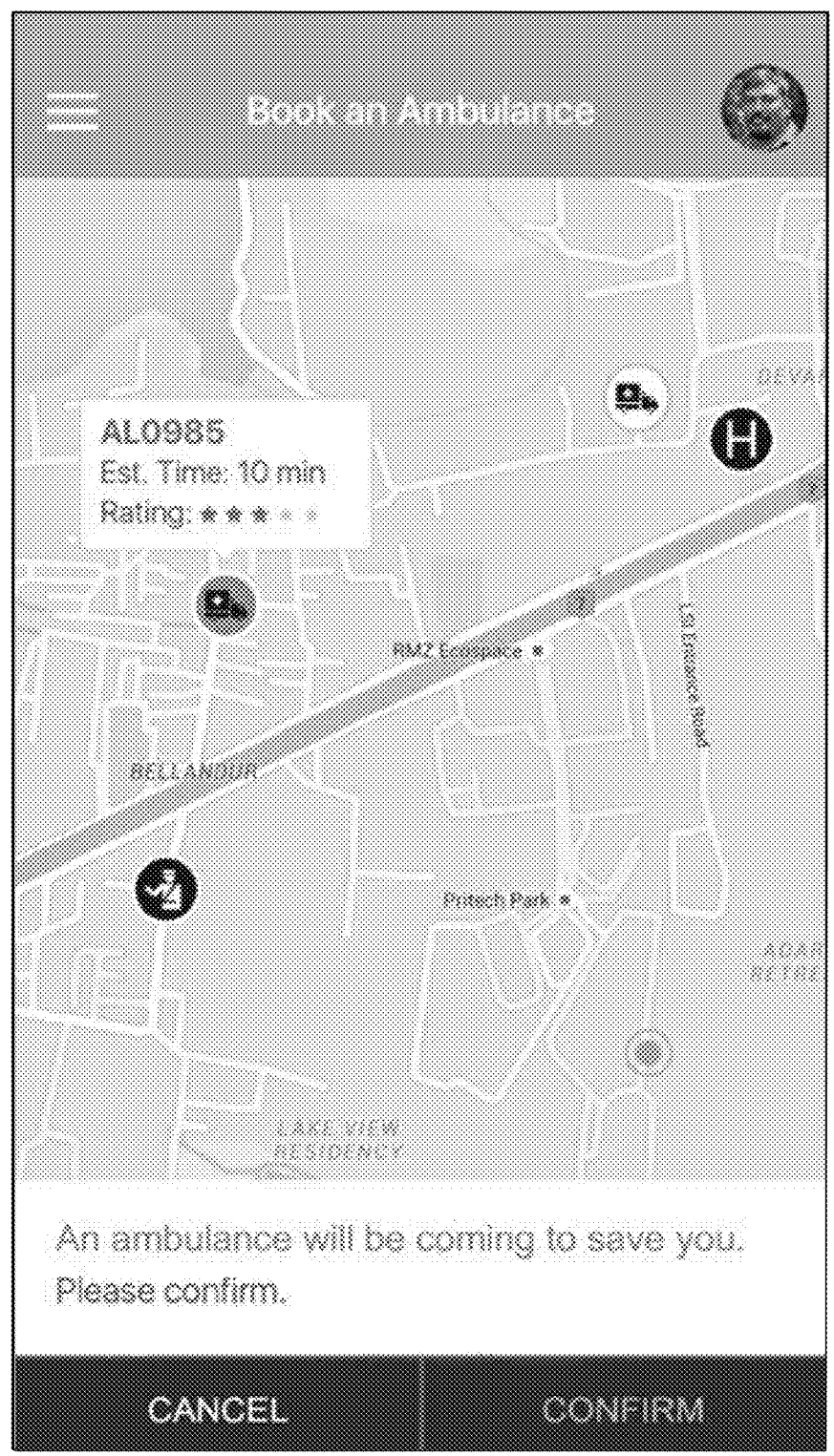
Figure 19:
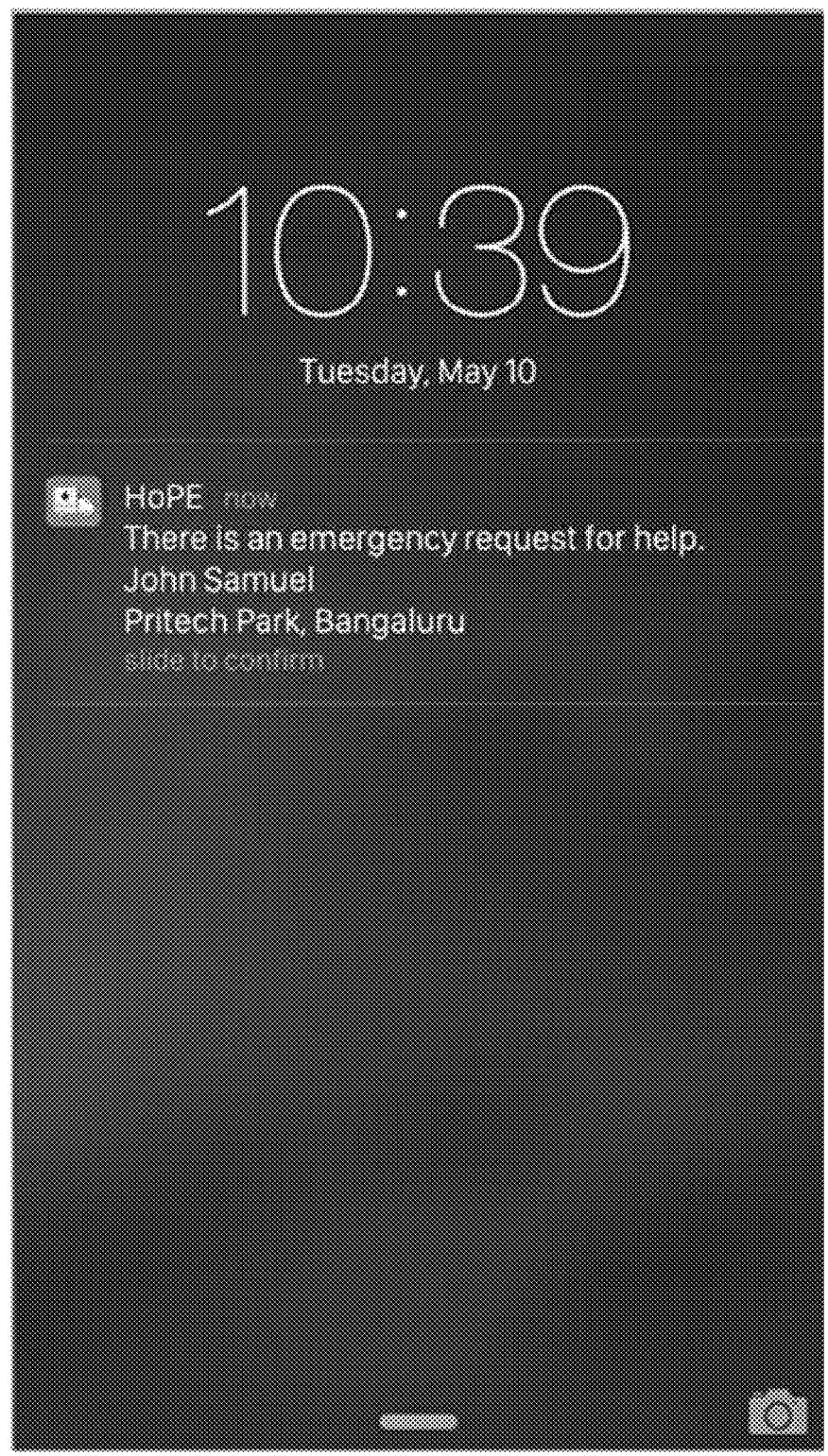

As further shown in FIG. 17, assume that the patient selects an ambulance identified as AL0985. Based on this selection, the user interface may indicate that this ambulance has been dispatched to the patient, as shown in FIG. 18. Additionally, or alternatively, integrated ambulance tracking system 210 may provide a message to ambulance operator device 225 of the selected ambulance, as shown in FIG. 19. For example, the message may indicate that a patient has requested pickup by the ambulance operator, may indicate the name of the patient, may indicate a location of patient device 220, may indicate a medical situation input by the patient, or the like. The ambulance operator may interact with ambulance operator device 225 to accept the patient request.

In some implementations, the ambulance operator may interact with ambulance operator device 225 to reject the patient request (e.g., if the ambulance operator has already been dispatched to the patient). In this case, integrated ambulance tracking system 210 may send a message to patient device 220, requesting that the patient select a different ambulance. Integrated ambulance tracking system 210 may provide information associated with the ambulances and/or hospitals to patient device 220 (e.g., excluding the dispatched ambulance), and patient device 220 may provide a user interface with this information, as described above. In some implementations, when integrated ambulance tracking system 210 dispatches an ambulance or receives information (e.g., from ambulance operator device 225) that the ambulance has been dispatched, integrated ambulance tracking system 210 may prevent information associated with the ambulance from being provided to other patient devices 220. In this way, integrated ambulance tracking system 210 may prevent an ambulance from being double-booked, and may conserve network resources by preventing unnecessary information and/or message from being sent.

Figure 20:
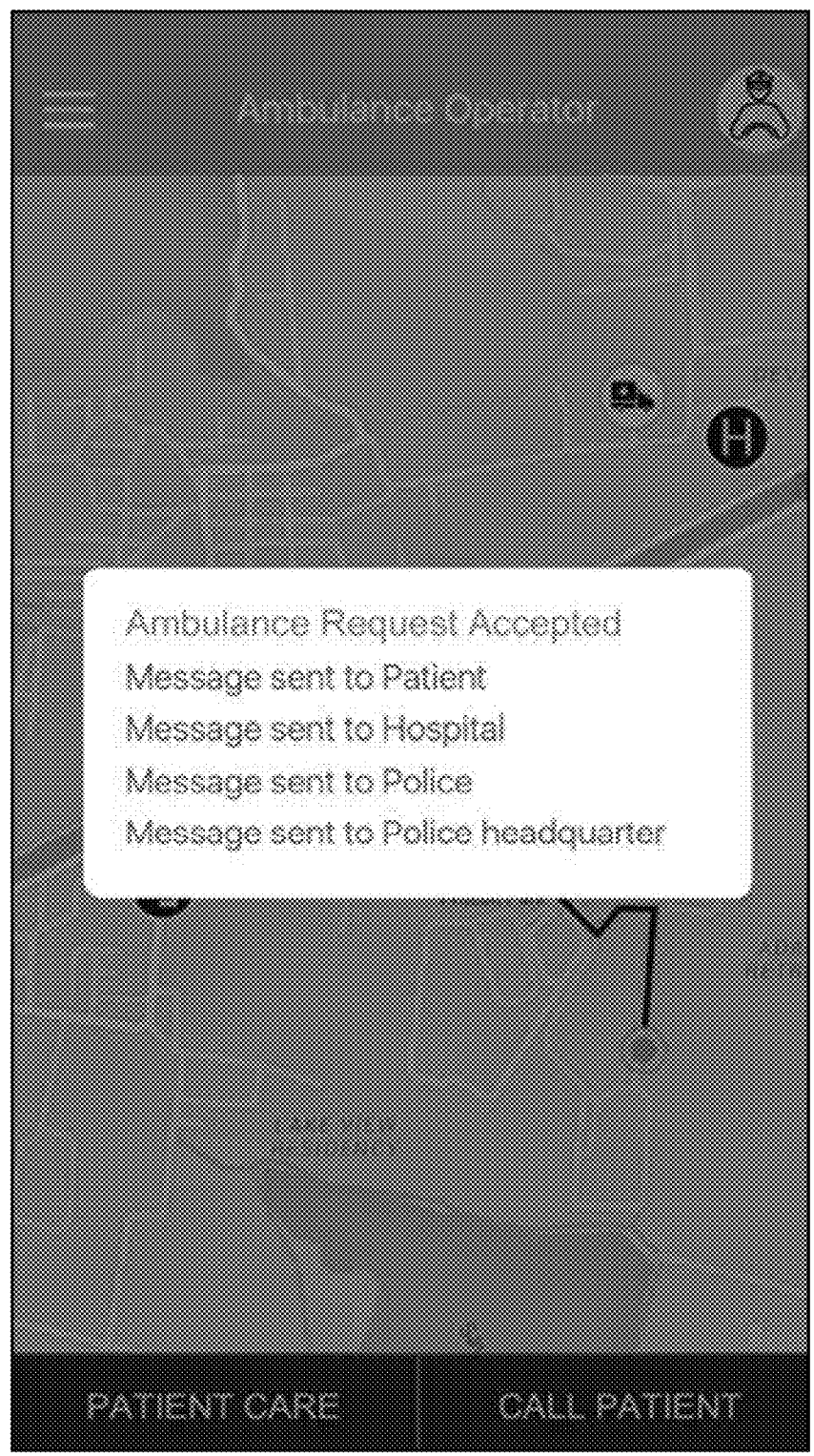

As shown in FIG. 20, integrated ambulance tracking system 210 may automatically coordinate sending of messages to various devices and parties when an ambulance is dispatched to a patient. For example, integrated ambulance tracking system 210 may send a message to patient device 220 indicating that the ambulance has been dispatched, indicating an amount of time until the ambulance arrives at patient device 220, indicating a route of the ambulance to patient device 220, or the like. In this way, integrated ambulance tracking system 210 may conserve network resources by providing updated information to patient device 220, which may reduce a quantity of calls placed to a 911 operator and/or may reduce a quantity of transmitted network messages. As another example, integrated ambulance tracking system 210 may send a message to police device 235 and/or police department device 240 indicating a route of the ambulance to patient device 220. In this way, police officers may be dispatched to clear a route and/or to assist with the patient. As another example, integrated ambulance tracking system 210 may send a message to hospital device 245 indicating a route of the ambulance to the hospital, patient information and/or medical information associated with the patient, a medical situation input by the patient, or the like. In this way, hospital staff may be prepared for intake and treatment of the patient.

Figure 21:
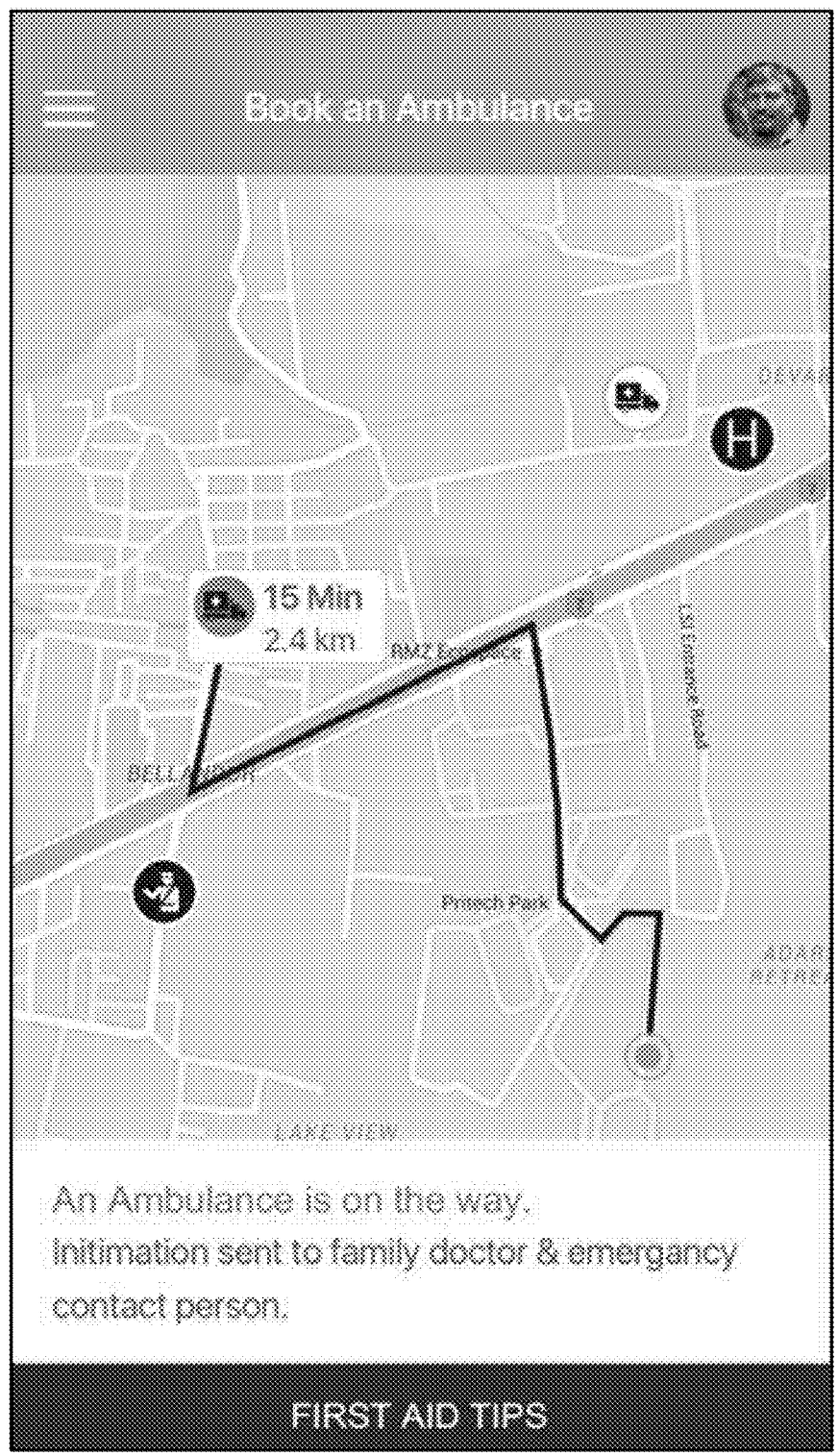

As shown in FIG. 21, information sent from integrated ambulance tracking system 210 to patient device 220 may confirm that an ambulance has been dispatched, may indicate a route from the ambulance to the patient, may indicate a distance from the ambulance to the patient, may indicate an estimated time for the ambulance to arrive at the patient, or the like. Additionally, or alternatively, the information may indicate that messages have been sent to contacts of the patient (e.g., to contact devices 250), and integrated ambulance tracking system 210 may send such messages to notify the contacts of the medical situation of the patient, to indicate that an ambulance has been dispatched to the patient, to identify a hospital to which the patient will be taken, to provide route information identifying a route to the patient or the hospital, or the like.

Figure 22:

As shown in FIG. 22, integrated ambulance tracking system 210 may provide first aid tips to patient device 220. In some implementations, the first aid information may indicate a variety of medical situations, and the patient may interact with patient device 220 to select a medical situation and receive first aid tips related to the medical situation. Additionally, or alternatively, integrated ambulance tracking system 210 may identify first aid tips related to a medical situation previously input by the patient, and may provide those first aid tips to patient device 220. In this way, integrated ambulance tracking system 210 ensures that patient device 220 receives the most relevant first aid tips, and may conserve network resources as compared to providing all first aid tips or more first aid tips than necessary.

Figure 23:
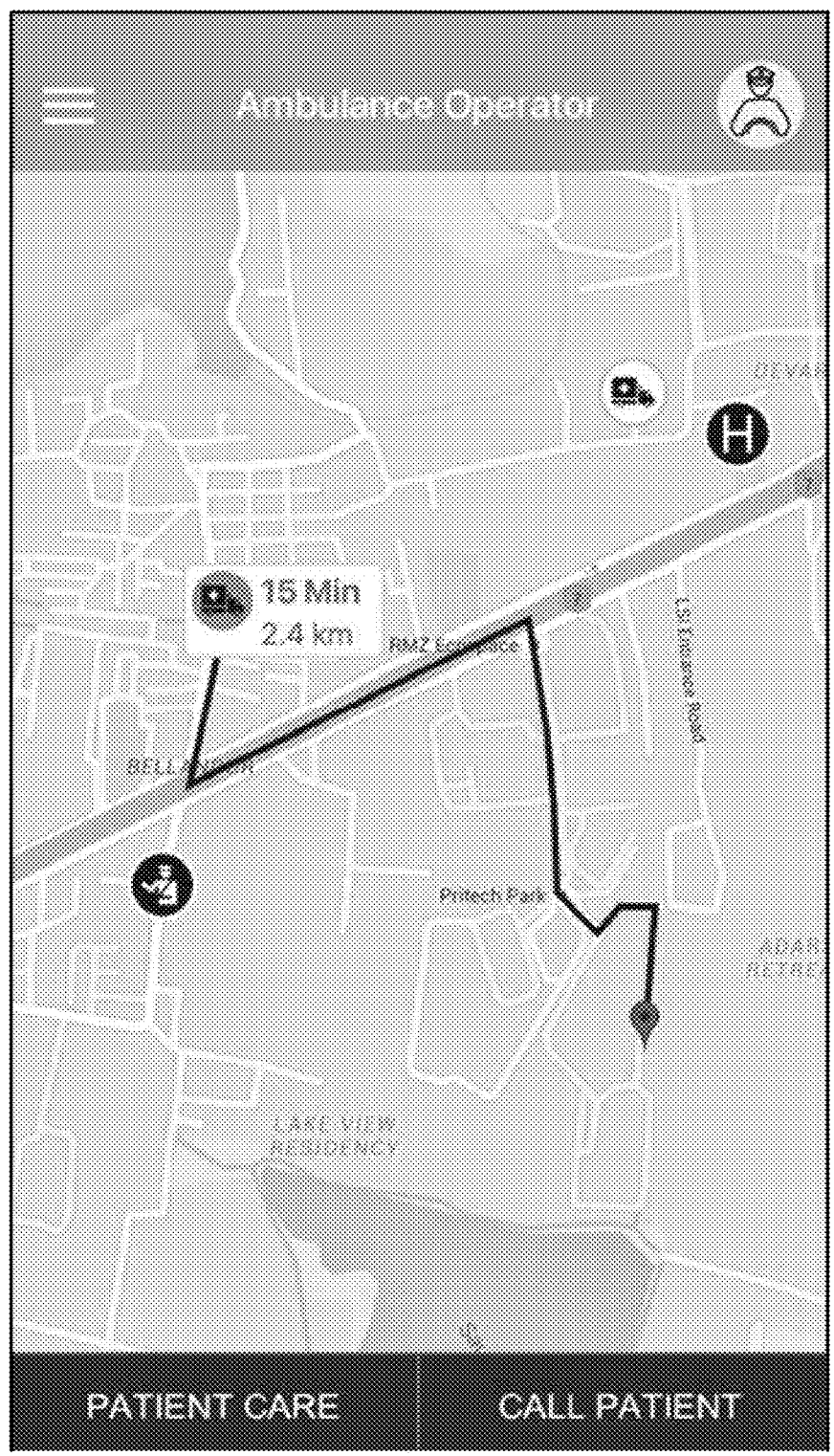

As shown in FIG. 23, information sent from integrated ambulance tracking system 210 to ambulance operator device 225 may indicate a route from the ambulance to the patient, may indicate a distance from the ambulance to the patient, may indicate an estimated time for the ambulance to arrive at the patient, may indicate a location of the patient, or the like. Additionally, or alternatively, information sent from integrated ambulance tracking system 210 to ambulance operator device 225 may include patient information to assist in patient care, information for contacting the patient (e.g., via a phone call), or the like.

Figure 24:
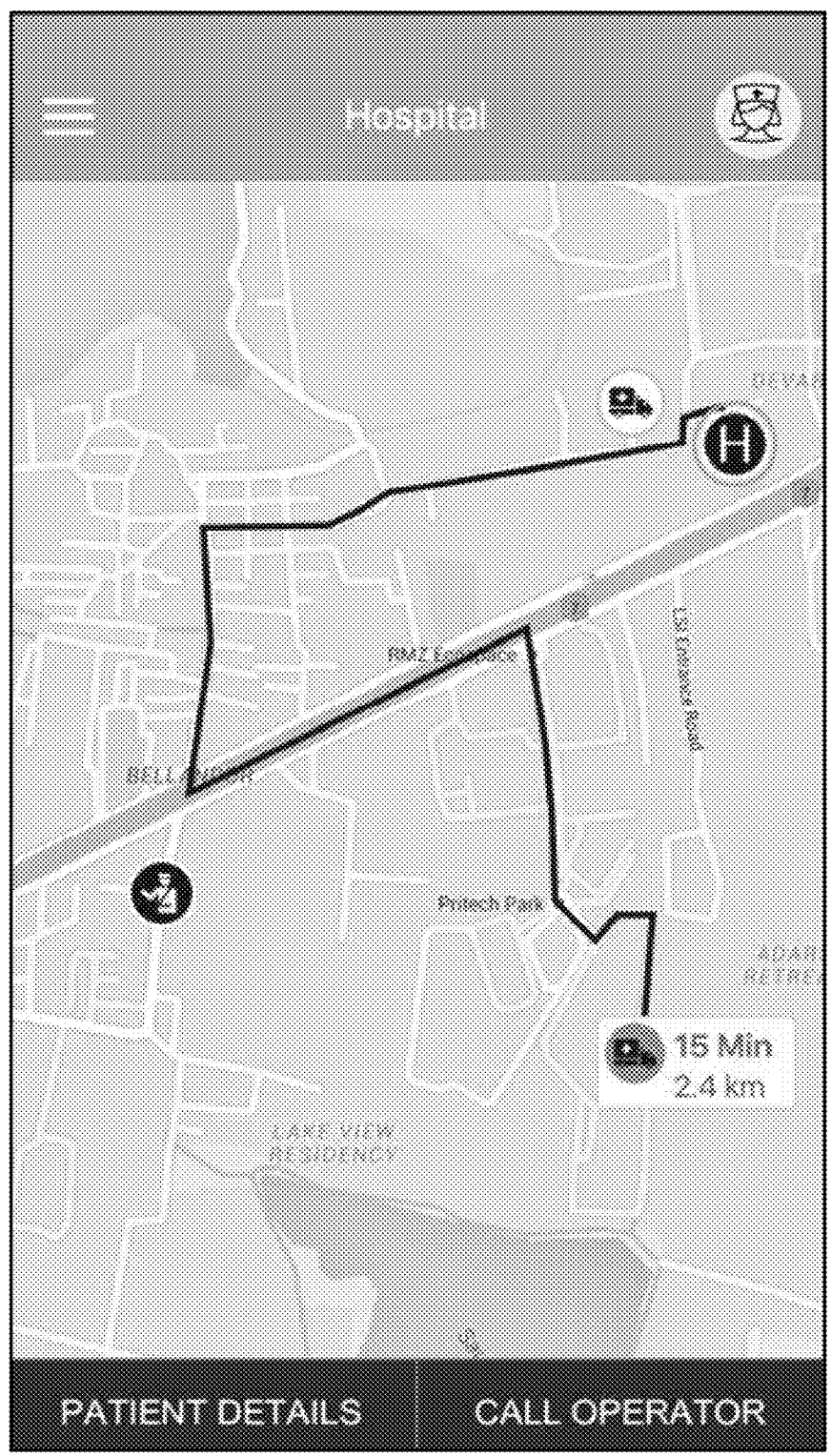

As shown in FIG. 24, information sent from integrated ambulance tracking system 210 to ambulance operator device 225 and/or hospital device 245 may indicate a route from the ambulance (or the patient) to the hospital, may indicate a distance from the ambulance to the hospital, may indicate an estimated time for the ambulance to arrive at the hospital, may indicate a location of the ambulance and/or hospital, or the like. Additionally, or alternatively, information sent from integrated ambulance tracking system 210 to hospital device 245 may include patient information to assist in patient care, information for contacting the ambulance operator (e.g., via a phone call), or the like.

Figure 25:
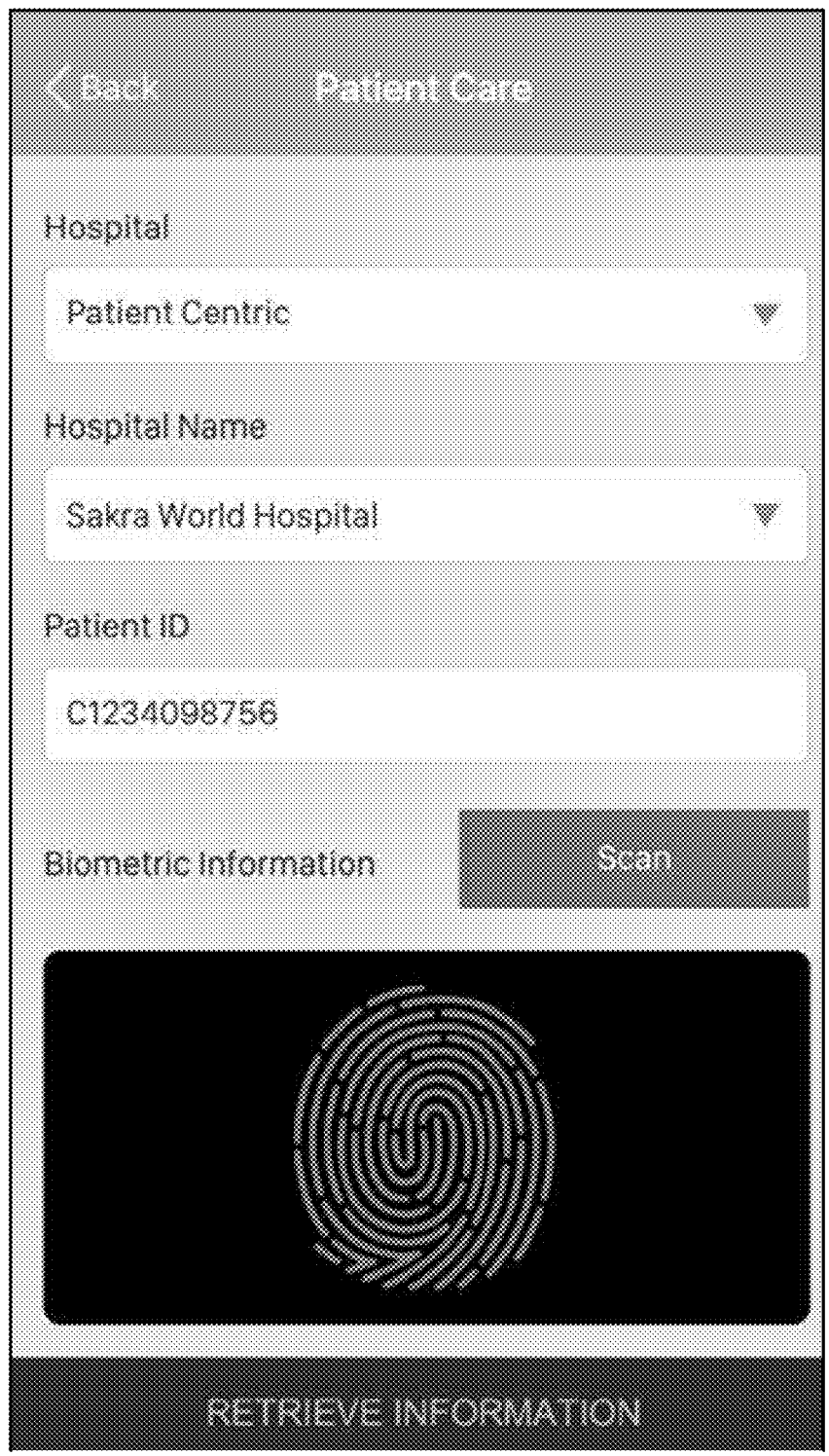

As shown in FIG. 25, an ambulance provider may interact with ambulance provider device 230 to input information to be sent to integrated ambulance tracking system 210. For example, an ambulance provider may indicate a hospital to which the information is to be sent. In some implementations, integrated ambulance tracking system 210 may automatically determine the hospital based on previously received information, based on identifying a hospital associated with an ambulance and/or the ambulance provider, or the like. As another example, the ambulance provider may provide input identifying the patient. In some implementations, integrated ambulance tracking system 210 may automatically identify the patient based on patient information. Additionally, or alternatively, the ambulance provider may obtain the patient identifier from the patient, and may input the patient identifier to ambulance provider device 230. Additionally, or alternatively, ambulance provider device 230 may use biometric information of the patient to identify the patient.

As shown in FIG. 26, the ambulance provider may interact with ambulance provider device 230 to input patient information, such as a patient name, a patient age, a patient blood type, a medication taken by the patient, information associated with doctors who have treated the patient, or the like. Additionally, or alternatively, ambulance provider device 230 may provide the patient identifier to integrated ambulance tracking system 210, and integrated ambulance tracking system 210 may identify medical information (e.g., EHR or EMR) of the patient using the patient identifier. Integrated ambulance tracking system 210 may provide the medical information to ambulance provider device 230 to assist the ambulance provider with patient care.

Figure 27:
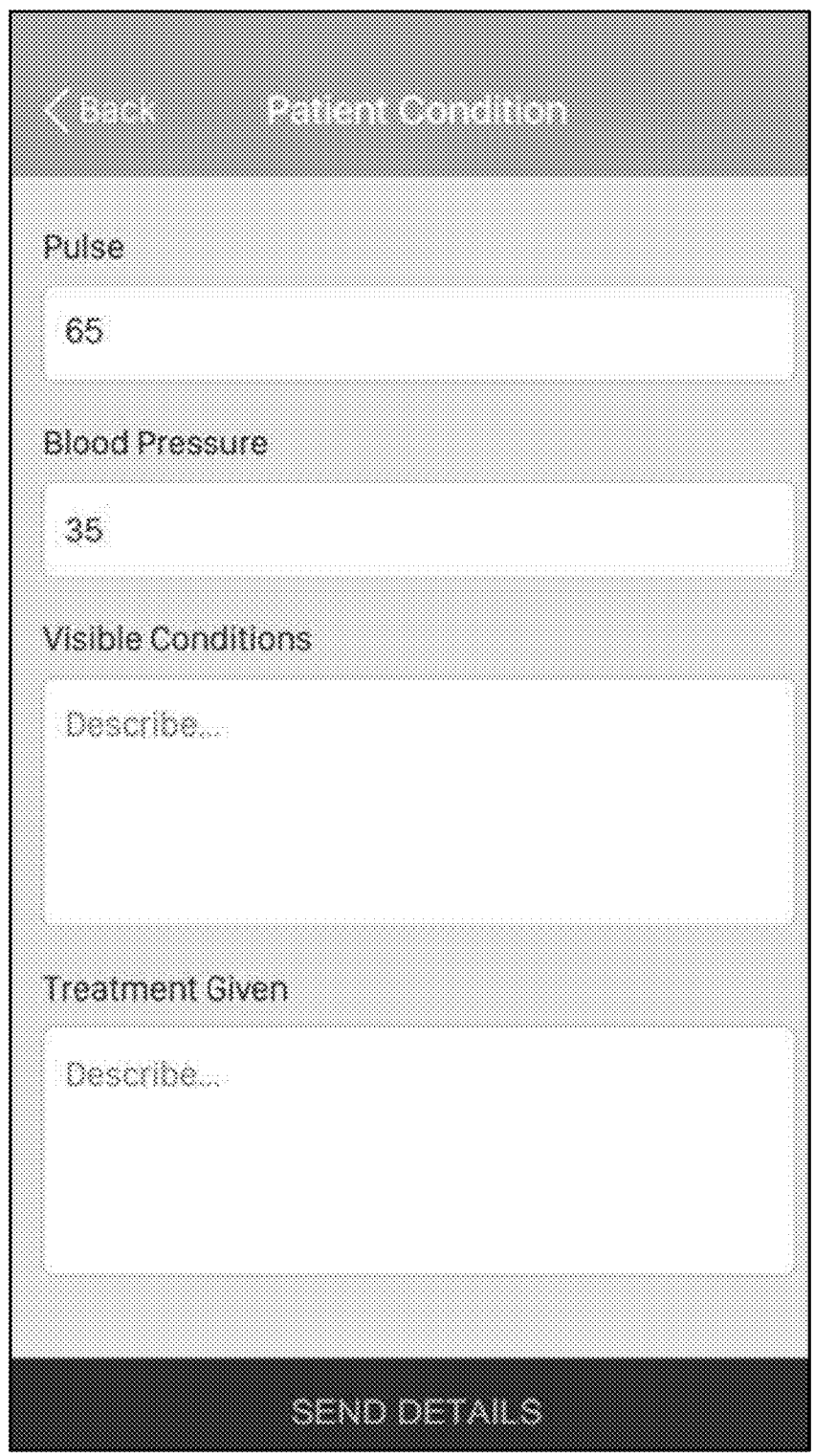

As shown in FIG. 27, the ambulance provider may interact with ambulance provider device 230 to input medical information and/or a medical situation of the patient, such as a pulse, a blood pressure, a medical condition, treatment information, or the like. As shown in FIG. 28, the ambulance provider may interact with ambulance provider device 230 to provide such information (e.g., described in connection with FIGS. 25-27) to a hospital to which the ambulance is destined (e.g., to hospital device 245 via integrated ambulance tracking system 210). Additionally, or alternatively, integrated ambulance tracking system 210 may send some information (e.g., medical information from an EHR or EMR, which may include all or a portion of the EHR or the EMR) to hospital device 245 without waiting for input from ambulance provider device 230. In this way, hospital staff may properly prepare to treat the patient upon arrival.

Figure 29:
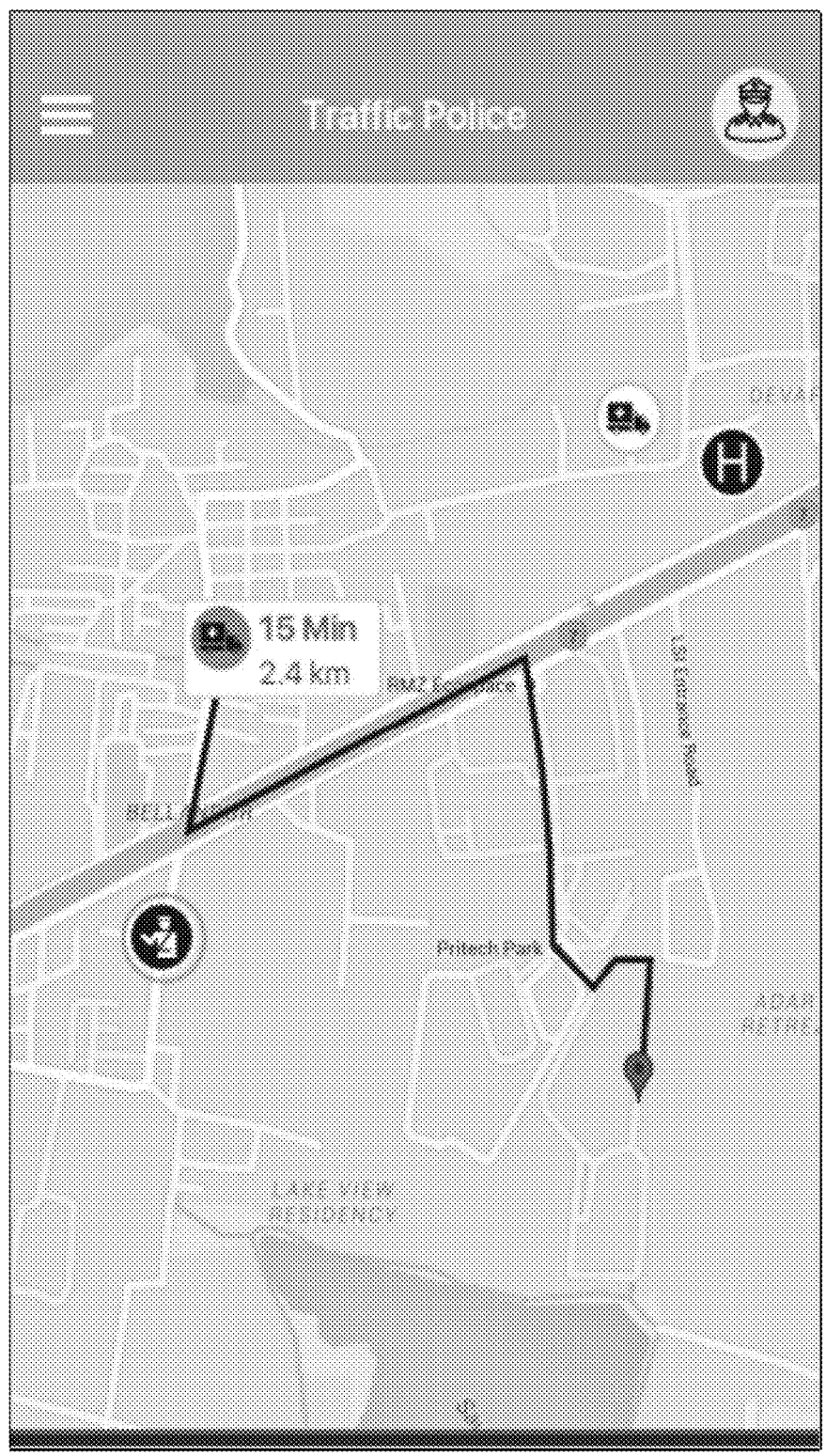
Figure 30:
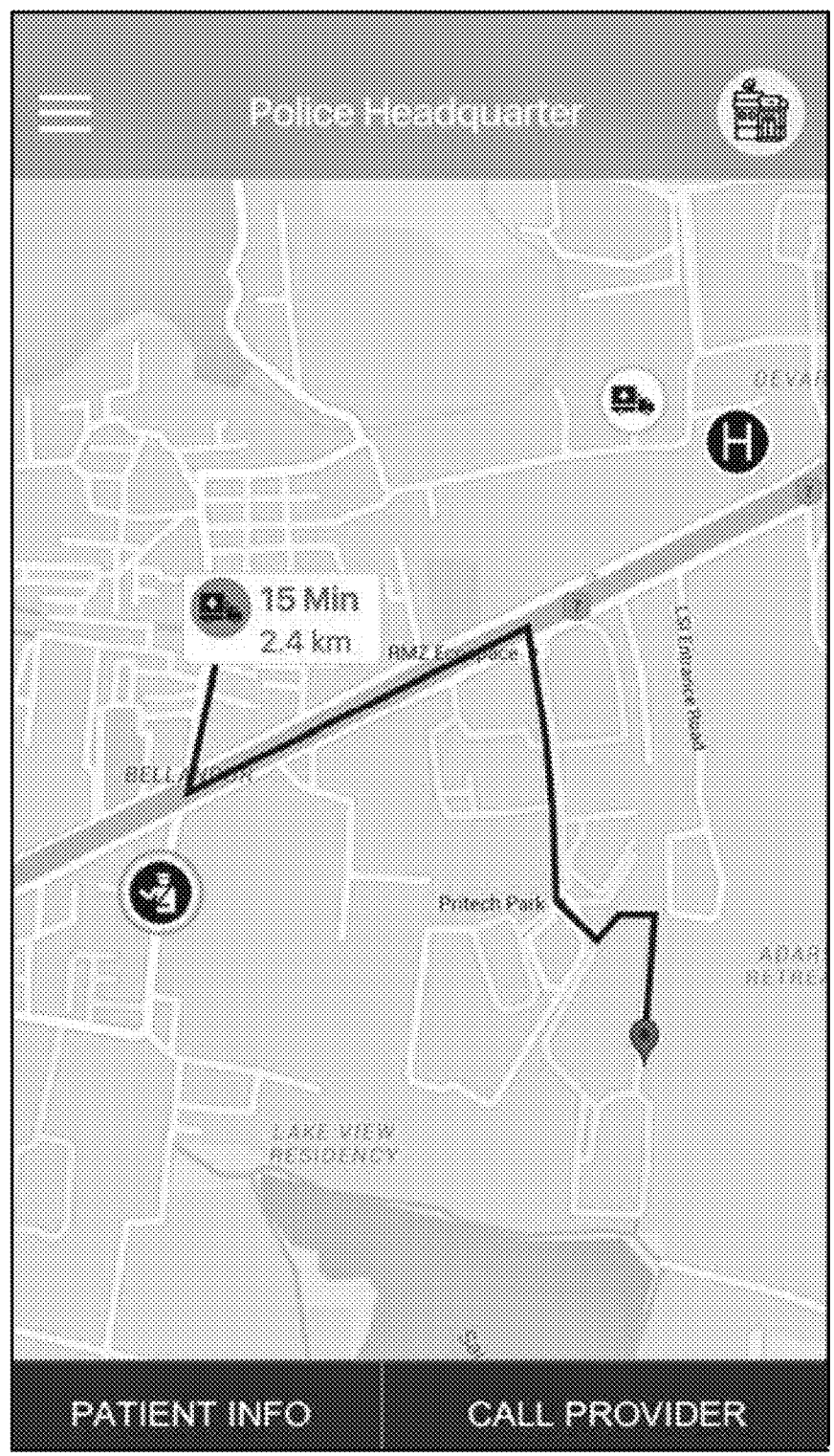

As shown in FIGS. 29 and 30, information sent from integrated ambulance tracking system 210 to police device 235 and/or police department device 240 may indicate a route from the ambulance to the patient and/or the hospital, may indicate a route from the patient to the hospital, may indicate a distance from the ambulance to the patient and/or the hospital, may indicate an estimated time for the ambulance to arrive at the patient and/or the hospital, may indicate a location of the ambulance, the patient and/or the hospital, or the like. Additionally, or alternatively, information sent from integrated ambulance tracking system 210 to police device 235 and/or police department device 240 may include patient information, information for contacting an ambulance operator and/or an ambulance provider (e.g., via a phone call), or the like. In some implementations, information sent from integrated ambulance tracking system 210 to police device 235 and/or police department device 240 may identify police officers within a threshold distance from the route of the ambulance (e.g., based on locations of police devices 235). In this way, police officers may be dispatched to assist in patient care, to assist with clearing a route from the ambulance to the patient or the hospital, or the like.

As indicated above, FIGS. 5-30 are provided as examples. Other examples are possible and may differ from what was described in connection with FIGS. 5-30.

Implementations described herein automatically provide appropriate information, associated with a medical situation, to various parties at the appropriate time, thereby reducing delays in patient care and ensuring proper preparation for patient care. Furthermore, implementations described herein conserves network resources and computing resources due to efficiencies associated with ensuring that appropriate information is provided to appropriate devices at appropriate times.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A system, comprising:
one or more memories; and
one or more processors, communicatively coupled to the one or more memories, to:
provide, to a first device associated with a patient, a user interface associated with an application,
the user interface providing one or more roles to be selected by a user of the application;
receive, from the first device, information associated with a selection of a role, of the one or more roles, associated with the patient;
receive, from the first device, a request for an ambulance;
determine, based on a location associated with the first device, one or more available ambulances within a geographical proximity of the location;
automatically select or provide for selection an available ambulance of the one or more available ambulances;
transmit, to a second device associated with an ambulance operator of the available ambulance, information that identifies the location associated with the first device;
identify a plurality of hospitals within a threshold distance to the patient;
generate a score for each of the plurality of hospitals, the score being generated based upon one or more of:
a medical situation associated with the patient,
registration information associated with the patient,
patient information associated with the patient,
a preference indicated by the patient, or
traffic conditions associated with a route to the plurality of hospitals;
determine a hospital, of the plurality of hospitals, to which the patient is to be delivered based on the score;
determine a route to be taken by the ambulance;
identify a set of traffic control devices along the route;
transmit, to the set of traffic control devices, instructions to further cause the set of traffic control devices to automate signal changing based on ambulance movement along the route; and
transmit, to a third device associated with the hospital, a notification that the available ambulance will be arriving with the patient,
the notification including an estimated arrival time.

2. The system of claim 1, where the one or more processors, when identifying the plurality of hospitals within the threshold distance to the patient, are to:
identify the plurality of hospitals within the threshold distance to the patient based on at least one of:
the location associated with the first device, or
information associating the plurality of hospitals within the threshold distance to the patient with the available ambulance.

3. The system of claim 1, where the one or more processors are further to:
generate a plurality of scores corresponding to a plurality of ambulances,
each score, of the plurality of scores corresponding to the plurality of ambulances, being generated based on a plurality of factors,
the plurality of factors including the location associated with the first device,
the plurality of ambulances including the available ambulance; and
where the one or more processors, when determining the available ambulance, are to:
determine the available ambulance based on the plurality of scores corresponding to the plurality of ambulances.

4. The system of claim 1, where the one or more processors are further to:
transmit, to the second device associated with the ambulance operator, information that identifies a fastest route to the first device or the patient.

5. The system of claim 1, where the one or more processors are further to:
transmit, to the second device associated with the ambulance operator, information that identifies a location of the hospital.

6. The system of claim 1, where the one or more processors are further to:
transmit, to the third device associated with the hospital, patient information associated with the patient.

7. The system of claim 1, where the one or more processors are further to:
identify a fourth device, associated with a police officer or a police department, based on the location associated with the first device; and
transmit, to the fourth device, route information associated with a route from the available ambulance to the patient.

8. The system of claim 1, where the one or more processors are further to:
identify a fourth device associated with an emergency contact of the patient; and
transmit, to the fourth device, a notification associated with the patient.

9. A non-transitory computer-readable medium storing instructions, the instructions comprising:
one or more instructions that, when executed by one or more processors, cause the one or more processors to:
provide, to a first device associated with a patient, a user interface associated with an application,
the user interface providing one or more roles to be selected by a user of the application;

receive, from the first device, information associated with a selection of a role, of the one or more roles, associated with the patient;
receive, from the first device, a request for a vehicle;
determine, based on a location associated with the first device one or more available vehicles within a geographical proximity of the location;
automatically select or provide for selection an available vehicle of the one or more available vehicles;
transmit, to a second device associated with a driver of the available vehicle, information that identifies a traffic route to the first device;
identify a plurality of destinations within a threshold distance to the user;
generate a score for each of the plurality of destinations,
 the score being generated based upon one or more of:
  a medical situation associated with the user,
  registration information associated with the user,
  patient information associated with the user,
  a preference indicated by the user, or
  traffic conditions associated with a route to the plurality of destinations;
determine a destination, of the plurality of destinations based on the score;
determine a route to be taken by the vehicle;
identify a set of traffic control devices along the route;
transmit instructions to the set of traffic control devices to further cause the set of traffic control devices to automate signal changing based on ambulance movement along the route; and
transmit, to a third device associated with the destination a notification that the available vehicle will be arriving with the user,
 the notification including an estimated arrival time.

10. The non-transitory computer-readable medium of claim 9, where the one or more instructions, when executed by the one or more processors, cause the one or more processors to:
transmit, to a fourth device associated with a passenger of the available vehicle, information associated with the user.

11. The non-transitory computer-readable medium of claim 9, where the one or more instructions, when executed by the one or more processors, cause the one or more processors to:
transmit, to a fourth device associated with a police officer or a police department, the information that identifies the traffic route.

12. The non-transitory computer-readable medium of claim 9, where the one or more instructions, when executed by the one or more processors, cause the one or more processors to:
transmit, to a fourth device associated with a contact of the user, a notification associated with the user.

13. The non-transitory computer-readable medium of claim 9, where the user is a patient, the available vehicle is an available ambulance, and the destination is a hospital.

14. A method performed by a system that includes one or more devices, the method comprising:
providing, to a patient device associated with a patient, a user interface associated with an application,
 the user interface providing one or more roles to be selected by a user of the application;
receiving, from the patient device, information associated with a selection of a role, of the one or more roles, associated with the patient;
receiving, by the system and from the patient device, a request for an ambulance;
determining, by the system and based on a location of the patient device, one or more available ambulances within a geographical proximity of the location;
automatically, by the system, selecting or providing for selection an available ambulance of the one or more available ambulances;
transmitting, by the system and to an ambulance operator device associated with an ambulance operator of the available ambulance, information associated with the location of the patient device;
identifying, by the system, a plurality of hospitals within a threshold distance to the patient;
generating, by the system, a score for each of the plurality of hospitals,
 the score being generated based upon one or more of:
  a medical situation associated with the patient,
  registration information associated with the patient,
  patient information associated with the patient,
  a preference indicated by the patient, or
  traffic conditions associated with a route to the plurality of hospitals,
determining, by the system, a hospital, of the plurality of hospitals, to which the ambulance is to deliver the patient based on the score;
determining, by the system, a route to be taken by the ambulance;
identifying, by the system, a set of traffic control devices along the route;
transmitting, by the system, instructions to the set of traffic control devices to further cause the set of traffic control devices to automate signal changing based on ambulance movement along the route; and
transmitting, by the system and to a hospital device associated with the hospital, a notification that the available ambulance will be arriving with the available ambulance or the patient,
 the notification including an estimated arrival time.

15. The method of claim 14, where transmitting the notification that the available ambulance will be arriving with the available ambulance or the patient comprises:
transmitting at least a portion of an electronic medical record or an electronic health record associated with the patient.

16. The method of claim 14, further comprising:
transmitting, to an ambulance provider device associated with an ambulance provider that travels with the ambulance, patient information associated with the patient.

17. The method of claim 14, further comprising:
identifying, based on the location of the patient device, a police device, associated with a police officer, or a police department device associated with a police department; and
transmitting, to the police device or the police department device, at least one of:
 information that identifies the location of the patient device,
 information that identifies a route from the available ambulance to the patient device, or
 information that identifies a route from the available ambulance to the hospital.

18. The non-transitory computer-readable medium of claim 9, where the one or more instructions, when executed by the one or more processors, cause the one or more processors to:

transmit, to the first device, a notification indicating that the available vehicle has been dispatched to the user.

19. The method of claim 14, further comprising:
transmitting, to the patient device, a notification indicating that the available ambulance has been dispatched to the patient.

20. The method of claim 14, further comprising:
transmitting, to the patient device, information associated with at least one of the ambulance or the hospital; and
receiving, from the patient device, a selection of at least one of the ambulance or the hospital.

* * * * *